United States Patent [19]

Baszcynski et al.

[11] Patent Number: 5,929,301
[45] Date of Patent: Jul. 27, 1999

[54] NUCLEIC ACID SEQUENCE ENCODING FLP RECOMBINASE

[75] Inventors: Christopher L. Baszcynski, Urbandale; Benjamin A. Bowen; Bruce J. Drummond, both of Des Moines; William J. Gordon-Kamm, Urbandale; David J. Peterson, Ames; Gary A. Sandahl, West Des Moines; Laura A. Tagliani, Ankeny; Zuo-Yu Zhao, Urbandale, all of Iowa

[73] Assignee: Pioneer Hi-Bred International, Johnston, Iowa

[21] Appl. No.: 08/972,258

[22] Filed: Nov. 18, 1997

[51] Int. Cl.$^6$ .............................. C12N 5/04; C12N 15/29; A01H 5/00; A01H 5/10
[52] U.S. Cl. .......................... 800/278; 800/278; 435/419; 47/58; 536/23.1
[58] Field of Search ............................ 435/419; 800/205, 800/250, DIG. 9, DIG. 56; 47/58; 536/23.1

[56] References Cited

FOREIGN PATENT DOCUMENTS 0 359 472  3/1990   European Pat. Off. .
91/16432   10/1991   WIPO .

OTHER PUBLICATIONS

Kilby et al. The Plant Journal. 1995. vol. 8: 639–652.
Lyznik et al. Nucleic Acid Research. 1993. vol. 21(4): 969–975.
Gordon–Kamm et al. Plant Cell. 1990. vol. 2: 603–618.
Ausubel et al. Short Protocols in Molecular Biology. John Wiley & Sons. 1989.
Murray, Elizabeth E., et al., "Codon Usage in Plant Genes," Nucleic Acids Research, 1989, pp. 477–498, vol. 17, No. 2.
Perlak, Frederick J., et al., "Modification of the Coding Sequence Enhances Plant Expression of Insect Control Protein Genes," Proc. Natl. Acad. Sci. USA, Apr. 1991, pp. 3324–3328, vol. 88.
Lloyd, Alan M., et al., "Functional expression of the yeast FLP/FRT site–specific recombination system in *Nicotiana tabacum*", Mol. Gen. Genet., 1994, pp. 653–657, vol. 242.
Lyznik, Leszek A., et al., "Heat–inducible expression of FLP gene in maize cells", *Plant Journal*, 1995, pp. 177–186, vol. 8(2).

*Primary Examiner*—Douglas W. Robinson
*Assistant Examiner*—Ousama M-Faiz Zaghmout
*Attorney, Agent, or Firm*—Alston & Bird LLP

[57] ABSTRACT

A nucleic acid sequence effectively expressing FLP recombinase in monocot plants, particularly in maize. Stable, transformed maize plants harboring a gene encoding FLP or harboring FRT nucleic acid sequences enable efficient site-directed recombination of nucleic acid sequences in a monocot's genome.

18 Claims, 2 Drawing Sheets

Figure 1

```
     ATGCCACAATTTGGTATATTATGTAAAACACCACCTAAGGTGCTTGTTCGTCAGTTTGTG
  1  |||| || || | || || || |||| || || ||||||| || | |||| ||    60
     ATGCCCCAGTTCGACATCCTCTGCAAGACCCCCCCAAGGTGCTCGTGAGGCAGTTCGTG
     M  P  Q  F  D  I  L  C  K  T  P  P  K  V  L  V  R  Q  F  V  -

GAAAGGTTTGAAAGACCTTCAGGTGAGAAAATAGCATTATGTGCTGCTGAACTAACCTAT
 61  || |||||| || || || || || ||||| || ||  || || || || || |||||  120
     GAGAGGTTCGAGAGGCCCTCCGGCGAGAAGATCGCCCTCTGCGCCGCCGAGCTCACCTAC
     E  R  F  E  R  P  S  G  E  K  I  A  L  C  A  A  E  L  T  Y  -

TTATGTTGGATGATTACACATAACGGAACAGCAATCAAGAGAGCCACATTCATGAGCTAT
121  || || |||||||| || || |||||| || || |||||| ||||| |||||| ||    180
     CTCTGCTGGATGATCACCCACAACGGCACCGCCATTAAGAGGGCCACCTTCATGTCATAC
     L  C  W  M  I  T  H  N  G  T  A  I  K  R  A  T  F  M  S  Y  -

AATACTATCATAAGCAATTCGCTGAGTTTCGATATTGTCAATAAATCACTCCAGTTTAAA
181  || || ||||||  ||| || ||   ||||| || || || || ||||||||| |||   240
     AACACCATCATCTCCAACTCCCTCTCCTTCGACATCGTGAACAAGTCCCTCCAGTTCAAA
     N  T  I  I  S  N  S  L  S  F  D  I  V  N  K  S  L  Q  F  K  -

TACAAGACGCAAAAAGCAACAATTCTGGAAGCCTCATTAAAGAAATTGATTCCTGCTTGG
241  |||||||| || || ||  || || |||| || || |||||||| | ||| || || || 300
     TACAAGACCCAGAAGGCCACCATCCTCGAGGCCTCCCTCAAGAAGCTCATCCCCGCCTGG
     Y  K  T  Q  K  A  T  I  L  E  A  S  L  K  K  L  I  P  A  W  -

GAATTTACAATTATTCCTTACTATGGACAAAAACATCAATCTGATATCACTGATATTGTA
301  || || || || || || || || |||| || || |||||| || || |||| || ||  360
     GAGTTCACCATCATCCCCTACTACGGCCAGAAGCACCAGTCCGACATCACCGACATCGTG
     E  F  T  I  I  P  Y  Y  G  Q  K  H  Q  S  D  I  T  D  I  V  -

AGTAGTTTGCAATTACAGTTCGAATCATCGGAAGAAGCAGATAAGGGAAATAGCCACAGT
361      | ||    | ||||||||| || || || || || || |||||| ||    ||||  420
     TCATCCCTCCAGCTTCAGTTCGAGTCCTCCGAGGAGGCTGACAAGGGCAACTCCCACTCC
     S  S  L  Q  L  Q  F  E  S  S  E  E  A  D  K  G  N  S  H  S  -

AAAAAAATGCTTAAAGCACTTCTAAGTGAGGGTGAAAGCATCTGGGAGATCACTGAGAAA
421  || || |||| ||  || || ||     ||||| ||    |||||||||||| |||||  480
     AAGAAGATGCTGAAGGCCCTCCTCTCCGAGGGCGAGTCCATCTGGGAGATCACCGAGAAG
     K  K  M  L  K  A  L  L  S  E  G  E  S  I  W  E  I  T  E  K  -

ATACTAAATTCGTTTGAGTATACTTCGAGATTTACAAAAACAAAAACTTTATACCAATTC
481  || || || || || || || || ||  || || || || || || || ||  || |||  540
     ATCCTCAACTCCTTCGAGTACACCTCCAGGTTCACTAAGACCAAGACCCTCTACCAGTTC
     I  L  N  S  F  E  Y  T  S  R  F  T  K  T  K  T  L  Y  Q  F  -

CTCTTCCTAGCTACTTTCATCAATTGTGGAAGATTCAGCGATATTAAGAACGTTGATCCG
541  |||||||| ||||| ||||| |||| ||| || || ||  || |||||| || || ||  600
     CTCTTCCTCGCCACCTTCATCAACTGCGGCAGGTTCTCAGACATCAAGAACGTGGACCCC
     L  F  L  A  T  F  I  N  C  G  R  F  S  D  I  K  N  V  D  P  -
```

```
     AAATCATTTAAATTAGTCCAAAATAAGTATCTGGGAGTAATAATCCAGTGTTTAGTGACA
601  || || || ||    ||  ||  ||   ||||| || || || ||  ||||||||  |  ||||| 660
     AAGTCCTTCAAGCTCGTGCAGAACAAGTACCTCGGCGTGATCATCCAGTGCCTCGTGACC
     K  S  F  K  L  V  Q  N  K  Y  L  G  V  I  I  Q  C  L  V  T  -

GAGACAAAGACAAGCGTTAGTAGGCACATATACTTCTTTAGCGCAAGGGGTAGGATCGAT
661  ||||| |||||  |||   |||||||||||| |||||||||  |||  | | ||||||||| 720
     GAGACCAAGACCTCCGTGTCCAGGCACATCTACTTCTTCTCCGCTCGCGGCAGGATCGAC
     E  T  K  T  S  V  S  R  H  I  Y  F  F  S  A  R  G  R  I  D  -

CCACTTGTATATTTGGATGAATTTTTGAGGAATTCTGAACCAGTCCTAAAACGAGTAAAT
721  || || || ||  ||| ||||||||| ||| ||||| || || || ||||| ||   || || 780
     CCCCTCGTGTACCTCGACGAGTTCCTCAGGAACTCAGAGCCCGTGCTCAAGAGGGTGAAC
     P  L  V  Y  L  D  E  F  L  R  N  S  E  P  V  L  K  R  V  N  -

AGGACCGGCAATTCTTCAAGCAATAAACAGGAATACCAATTATTAAAAGATAACTTAGTC
781  |||||||||| || ||   |||  ||  |||||  ||||  |  |||  |||  ||| ||| 840
     AGGACCGGCAACTCCTCCTCCAACAAGCAGGAGTACCAGCTCCTCAAGGACAACCTCGTG
     R  T  G  N  S  S  N  K  Q  E  Y  Q  L  L  K  D  N  L  V  -

AGATCGTACAATAAAGCTTTGAAGAAAAATGCGCCTTATTCAATCTTTGCTATAAAAAAT
841  || || |||||| || ||  | |||||| || || ||||| |||| || || || || || 900
     AGGTCCTACAACAAGGCCCTCAAGAAGAACGCCCCCTACTCCATCTTCGCCATCAAGAAC
     R  S  Y  N  K  A  L  K  K  N  A  P  Y  S  I  F  A  I  K  N  -

GGCCCAAAATCTCACATTGGAAGACATTTGATGACCTCATTTCTTTCAATGAAGGGCCTA
901  ||||| |||| || |||||||| || || | |||||| ||  || || |||||||||||| 960
     GGCCCCAAGTCCCACATCGGTAGGCACCTCATGACCTCCTTCCTCTCAATGAAGGGCCTC
     G  P  K  S  H  I  G  R  H  L  M  T  S  F  L  S  M  K  G  L  -

ACGGAGTTGACTAATGTTGTGGGAAATTGGAGCGATAAGCGTGCTTCTGCCGTGGCCAGG
961  || ||| || || || ||||| ||  || ||  ||| ||| || ||| ||||||||||| 1020
     ACCGAGCTCACCAACGTGGTGGGCAACTGGTCCGACAAGAGGGCCTCCGCCGTGGCCAGG
     T  E  L  T  N  V  V  G  N  W  S  D  K  R  A  S  A  V  A  R  -

ACAACGTATACTCATCAGATAACAGCAATACCTGATCACTACTTCGCACTAGTTTCTCGG
1021 || || || || || || |||||  ||| || || ||||  || || || |||| ||  | 1080
     ACCACCTACACCCACCAGATCACCGCCATCCCCGACCACTACTTCGCCCTCGTGTCAAGG
     T  T  Y  T  H  Q  I  T  A  I  P  D  H  Y  F  A  L  V  S  R  -

TACTATGCATATGATCCAATATCAAAGGAAATGATAGCATTGAAGGATGAGACTAATCCA
1081 ||||| ||  || || ||  || || || || ||| | || |||||| |||||||| || 1140
     TACTACGCCTACGACCCCATCTCCAAGGAGATGATCGCCCTCAAGGACGAGACTAACCCC
     Y  Y  A  Y  D  P  I  S  K  E  M  I  A  L  K  D  E  T  N  P  -

ATTGAGGAGTGGCAGCATATAGAACAGCTAAAGGGTAGTGCTGAAGGAAGCATACGATAC
1141 || ||||||||||||| || ||  |||| |||||| || ||  || ||  ||| | ||| 1200
     ATCGAGGAGTGGCAGCACATCGAGCAGCTCAAGGGCTCCGCCGAGGGCTCCATCAGGTAC
     I  E  E  W  Q  H  I  E  Q  L  K  G  S  A  E  G  S  I  R  Y  -

CCCGCATGGAATGGGATAATATCACAGGAGGTACTAGACTACCTTTCATCCTACATAAAT
1201 |||||  || ||| || || ||  |||||||| || ||||||| || || || ||| || 1260
     CCCGCCTGGAACGGCATCATCTCCCAGGAGGTGCTCGACTACCTCTCCTCCTACATCAAC
     P  A  W  N  G  I  I  S  Q  E  V  L  D  Y  L  S  S  Y  I  N  -

AGACGCATATAA
1261 ||   | | | |  1272
     AGGAGGATCTGA
     R  R  I  *
```

5,929,301

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1272 base pairs (B) TYPE: nucleic acid
           (C) STRANDEDNESS: double
           (D) TOPOLOGY: linear (ii) MOLECULE TYPE: DNA (genomic)

(vi) ORIGINAL SOURCE:
           (A) ORGANISM: Synthetic sequence (optimized)

(xi) SEQUENCE DESCRIPTION: SEQ ID NO:1:

```
ATGCCCCAGT TCGACATCCT CTGCAAGACC CCCCCCAAGG TGCTCGTGAG GCAGTTCGTG        60

GAGAGGTTCG AGAGGCCCTC CGGCGAGAAG ATCGCCCTCT GCGCCGCCGA GCTCACCTAC       120

CTCTGCTGGA TGATCACCCA CAACGGCACC GCCATTAAGA GGGCCACCTT CATGTCATAC       180

AACACCATCA TCTCCAACTC CCTCTCCTTC GACATCGTGA ACAAGTCCCT CCAGTTCAAA       240

TACAAGACCC AGAAGGCCAC CATCCTCGAG GCCTCCCTCA GAAGCTCAT CCCCGCCTGG        300

GAGTTCACCA TCATCCCCTA CTACGGCCAG AAGCACCAGT CCGACATCAC CGACATCGTG       360

TCATCCCTCC AGCTTCAGTT CGAGTCCTCC GAGGAGGCTG ACAAGGGCAA CTCCCACTCC       420

AAGAAGATGC TGAAGGCCCT CCTCTCCGAG GGCGAGTCCA TCTGGGAGAT CACCGAGAAG       480

ATCCTCAACT CCTTCGAGTA CACCTCCAGG TTCACTAAGA CCAAGACCCT CTACCAGTTC       540

CTCTTCCTCG CCACCTTCAT CAACTGCGGC AGGTTCTCAG ACATCAAGAA CGTGGACCCC       600

AAGTCCTTCA AGCTCGTGCA GAACAAGTAC CTCGGCGTGA TCATCCAGTG CCTCGTGACC       660

GAGACCAAGA CCTCCGTGTC CAGGCACATC TACTTCTTCT CCGCTCGCGG CAGGATCGAC       720

CCCCTCGTGT ACCTCGACGA GTTCCTCAGG AACTCAGAGC CCGTGCTCAA GAGGGTGAAC       780

AGGACCGGCA ACTCCTCCTC CAACAAGCAG GAGTACCAGC TCCTCAAGGA CAACCTCGTG       840

AGGTCCTACA CAAGGCCCT CAAGAAGAAC GCCCCCTACT CCATCTTCGC CATCAAGAAC        900

GGCCCCAAGT CCCACATCGG TAGGCACCTC ATGACCTCCT TCCTCTCAAT GAAGGGCCTC       960

ACCGAGCTCA CCAACGTGGT GGGCAACTGG TCCGACAAGA GGGCCTCCGC CGTGGCCAGG      1020

ACCACCTACA CCCACCAGAT CACCGCCATC CCCGACCACT ACTTCGCCCT CGTGTCAAGG      1080

TACTACGCCT ACGACCCCAT CTCCAAGGAG ATGATCGCCC TCAAGGACGA GACTAACCCC      1140

ATCGAGGAGT GGCAGCACAT CGAGCAGCTC AAGGGCTCCG CCGAGGGCTC CATCAGGTAC      1200

CCCGCCTGGA ACGGCATCAT CTCCCAGGAG GTGCTCGACT ACCTCTCCTC CTACATCAAC      1260

AGGAGGATCT GA                                                         1272
```

(2) INFORMATION FOR SEQ ID NO:2:

(i) SEQUENCE CHARACTERISTICS:
          (A) LENGTH: 423 amino acids
          (B) TYPE: amino acid
          (C) STRANDEDNESS: Not Relevant
          (D) TOPOLOGY: linear (ii) MOLECULE TYPE: protein (vi) ORIGINAL SOURCE:
           (A) ORGANISM: Saccharomyces cerevisiae (xi) SEQUENCE DESCRIPTION: SEQ ID NO:2:

```
    Met Pro Gln Phe Asp Ile Leu Cys Lys Thr Pro Pro Lys Val Leu Val
    1               5                  10                  15

Arg Gln Phe Val Glu Arg Phe Glu Arg Pro Ser Gly Glu Lys Ile Ala
                20                  25                  30

Leu Cys Ala Ala Glu Leu Thr Tyr Leu Cys Trp Met Ile Thr His Asn
            35                  40                  45
```

```
Gly Thr Ala Ile Lys Arg Ala Thr Phe Met Ser Tyr Asn Thr Ile Ile
 50                  55                  60

Ser Asn Ser Leu Ser Phe Asp Ile Val Asn Lys Ser Leu Gln Phe Lys
 65                  70                  75                  80

Tyr Lys Thr Gln Lys Ala Thr Ile Leu Glu Ala Ser Leu Lys Lys Leu
                 85                  90                  95

Ile Pro Ala Trp Glu Phe Thr Ile Ile Pro Tyr Tyr Gly Gln Lys His
                100                 105                 110

Gln Ser Asp Ile Thr Asp Ile Val Ser Ser Leu Gln Leu Gln Phe Glu
                115                 120                 125

Ser Ser Glu Glu Ala Asp Lys Gly Asn Ser His Ser Lys Lys Met Leu
130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
                180                 185                 190

Ser Asp Ile Lys Asn Val Asp Pro Lys Ser Phe Lys Leu Val Gln Asn
                195                 200                 205

Lys Tyr Leu Gly Val Ile Ile Gln Cys Leu Val Thr Glu Thr Lys Thr
210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Asn Lys Gln Glu Tyr
                260                 265                 270

Gln Leu Leu Lys Asp Asn Leu Val Arg Ser Tyr Asn Lys Ala Leu Lys
                275                 280                 285

Lys Asn Ala Pro Tyr Ser Ile Phe Ala Ile Lys Asn Gly Pro Lys Ser
290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
                340                 345                 350

His Tyr Phe Ala Leu Val Ser Arg Tyr Tyr Ala Tyr Asp Pro Ile Ser
                355                 360                 365

Lys Glu Met Ile Ala Leu Lys Asp Glu Thr Asn Pro Ile Glu Glu Trp
                370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile
                420
```

(2) INFORMATION FOR SEQ ID NO:3:

(i) SEQUENCE CHARACTERISTICS:
        (A) LENGTH: 1272 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
              (A) ORGANISM: Saccharomyces cerevisiae (xi) SEQUENCE DESCRIPTION: SEQ ID NO:3:

```
ATGCCACAAT TTGGTATATT ATGTAAAACA CCACCTAAGG TGCTTGTTCG TCAGTTTGTG        60

GAAAGGTTTG AAAGACCTTC AGGTGAGAAA ATAGCATTAT GTGCTGCTGA ACTAACCTAT       120

TTATGTTGGA TGATTACACA TAACGGAACA GCAATCAAGA GAGCCACATT CATGAGCTAT       180

AATACTATCA TAAGCAATTC GCTGAGTTTC GATATTGTCA ATAAATCACT CCAGTTTAAA       240

TACAAGACGC AAAAAGCAAC AATTCTGGAA GCCTCATTAA AGAAATTGAT TCCTGCTTGG       300

GAATTTACAA TTATTCCTTA CTATGGACAA AAACATCAAT CTGATATCAC TGATATTGTA       360

AGTAGTTTGC AATTACAGTT CGAATCATCG GAAGAAGCAG ATAAGGGAAA TAGCCACAGT       420

AAAAAAATGC TTAAAGCACT TCTAAGTGAG GGTGAAAGCA TCTGGGAGAT CACTGAGAAA       480

ATACTAAATT CGTTTGAGTA TACTTCGAGA TTTACAAAAA CAAAAACTTT ATACCAATTC       540

CTCTTCCTAG CTACTTTCAT CAATTGTGGA AGATTCAGCG ATATTAAGAA CGTTGATCCG       600

AAATCATTTA AATTAGTCCA AAATAAGTAT CTGGGAGTAA TAATCCAGTG TTTAGTGACA       660

GAGACAAAGA CAAGCGTTAG TAGGCACATA TACTTCTTTA GCGCAAGGGG TAGGATCGAT       720

CCACTTGTAT ATTTGGATGA ATTTTTGAGG AATTCTGAAC CAGTCCTAAA ACGAGTAAAT       780

AGGACCGGCA ATTCTTCAAG CAATAAACAG GAATACCAAT TATTAAAAGA TAACTTAGTC       840

AGATCGTACA ATAAAGCTTT GAAGAAAAAT GCGCCTTATT CAATCTTTGC TATAAAAAAT       900

GGCCCAAAAT CTCACATTGG AAGACATTTG ATGACCTCAT TTCTTTCAAT GAAGGGCCTA       960

ACGGAGTTGA CTAATGTTGT GGGAAATTGG AGCGATAAGC GTGCTTCTGC CGTGGCCAGG      1020

ACAACGTATA CTCATCAGAT AACAGCAATA CCTGATCACT ACTTCGCACT AGTTTCTCGG      1080

TACTATGCAT ATGATCCAAT ATCAAAGGAA ATGATAGCAT TGAAGGATGA GACTAATCCA      1140

ATTGAGGAGT GGCAGCATAT AGAACAGCTA AAGGGTAGTG CTGAAGGAAG CATACGATAC      1200

CCCGCATGGA ATGGGATAAT ATCACAGGAG GTACTAGACT ACCTTTCATC CTACATAAAT      1260

AGACGCATAT AA                                                         1272
```

(2) INFORMATION FOR SEQ ID NO:4:

(i) SEQUENCE CHARACTERISTICS:
              (A) LENGTH: 34 base pairs
              (B) TYPE: nucleic acid
              (C) STRANDEDNESS: double
              (D) TOPOLOGY: linear (vi) ORIGINAL SOURCE:
              (A) ORGANISM: Saccharomyces cerevisiae (xi) SEQUENCE DESCRIPTION: SEQ ID NO:4:

```
GAAGTTCCTA TTCTCTAGAA AGTATAGGAA CTTC                                    34
```

NUCLEIC ACID SEQUENCE ENCODING FLP RECOMBINASE

FIELD OF THE INVENTION

The invention relates to the modification of plant genomes, particularly to compositions and methods for the excision of nucleotide sequences that have been incorporated into the genome.

BACKGROUND OF THE INVENTION

*Saccharomyces cerevisiae* harbor an autonomously replicating 2T plasmid containing the gene FLPy. FLPy encodes the protein, FLP, a site-specific recombinase acting at defined FLP-recognition targets, FRTs.

Like the cre/lox bacterial system, the yeast FLP/FRT system has been suggested as providing a useful and efficient method for inserting or excising genes in a genome of choice. However, in practice, the yeast FLP nucleic acid sequence (FLPy) does not efficiently express active recombinase in plant cells. For example, in experiments with suspension cells and callus, FLP-transformed maize cells produced only a very low frequency of detectable excision events. See, for example, Lyznik et al., (1993), *Nucleic Acids Research* 21:969–975 and the Examples below. Furthermore, it has not previously been demonstrated that the FRT/FLP system functions in monocot plants, or that FRT or FLP are inheritable and functional in the progeny of monocot plants.

It would therefore be very beneficial to provide an FLP nucleic acid sequence that would efficiently produce an effective FLP recombinase in monocot plant cells, particularly in maize cells. Such an effective FLP would permit use of FLP recombinase to selectively and reliably modulate gene excision events in a plant cell genome. It would also be very useful to provide monocot plants stably transformed with FRT nucleic acid sequences, FLP nucleic acid sequences, or both, capable of producing high frequency recombination events, which stably transformed plants pass the FRT/FLP nucleic acid sequences and active recombinase to subsequent generations.

SUMMARY OF THE INVENTION

Compositions and methods for modification of plant genomes are provided. The compositions comprise FLP recombinase sequences that have been modified for enhanced expression in plants. The compositions are useful for excision of sequences from the plant genome.

In one embodiment the FLP recombinase is modified for enhanced expression in maize. This specific nucleic acid sequence, moFLP (Sequence ID. NO: 1) is based on the native, yeast FLP. moFLP efficiently encodes active FLP recombinase (Sequence ID. NO: 2) in monocot plant cells, particularly in maize cells. Monocot plants, particularly maize plants, are stably transformed with moFLP, and successfully pass the gene onto succeeding generations with full expression and activity. Maize plants stably carrying FRT sequences are also provided, which FRT-containing plants pass these FRT nucleic acid sequences onto succeeding generations. Transgenic monocot plants expressing moFLP and containing FRT nucleic acid sequences are capable of producing a high frequency of recombination events (i.e. excision).

Hybrid plants are formed by genetically crossing a plant stably expressing moFLP with a plant stably containing FRT sequences. In such hybrid plants, expression of moFLP permits FLP-mediated recombination events at the FRT sequences.

Transformed plants carrying the nucleic acid sequence of at least one FRT site are modified to excise a nucleic acid sequence from between two FRT sites, by inducing expression of moFLP in the plant's genome. Such expression is induced by transfecting the plant's cells with moFLP, or by inducing expression of moFLP from the plant's genome. Induced expression can be via an inducible promoter.

BRIEF DESCRIPTION OF THE FIGURES

FIG. 1 provides a comparison of an optimized sequence of the FLP recombinase with the native yeast sequence.

DETAILED DESCRIPTION OF THE INVENTION

Novel nucleotide sequences modified for enhanced expression in plants are provided. The nucleotide sequences encode a FLP recombinase that provides functional FLP recombinase activity in the plants.

Expression of the FLP recombinase in a plant cell comprising a target sequence with flanking FRT sites directs efficient gene excision of the target sequence. In this manner, methods are provided for removing unwanted sequences from a plant genome after the sequence has served its usefulness.

moFLP

The nucleic acid sequence encoding yeast FLP recombinase was modified for enhanced expression in monocots, and particularly for efficient expression in maize. See, for example the nucleic acid sequence (moFLP) shown in FIG. 1 compared with the yeast FLP nucleic acid sequence (FLPy) (Sequence ID. NO. 3). The 423 amino acid protein sequence of FLP is also shown (Sequence ID. NO:2). Recently, a revised sequence for FLPy was published, making a single base change at nucleic acid 14 from A to G. This creates a single amino acid change in the FLP protein at amino acid 5 from D to G. Compared to the originally published yeast sequence; see Hartley et al. (1980)*Nature* 286: 860–864.

While the moFLP nucleic acid sequence shown in FIG. 1 includes preferred codons for expression of amino acids in maize, it is understood that a useful sequence may contain codons occurring in maize with less than the highest reported maize codon frequencies. For example, those codons having a frequency in maize of greater than about 20% need not be altered to attain an increased efficiency over the yeast sequence. In the preferred embodiment, all of the yeast sequence codons having a frequency in maize of less than 20% are changed to codons having a frequency of greater than 20%, using information on maize codon usage such as that from Murray et al. (1989) *Nucl. Acids Res.* 17(2):477–498 and from Fennoy et al. (1993) *Nucl. Acids Res.* 21(23)5294–5300. A preferred sequence is the modified sequence shown in FIG. 1, moFLP, Seq. ID NO: 1.

In this manner, sequences can be partially modified, substantially modified or completely modified. That is, sequences can be constructed containing at least 40% modified codons, preferably at least 60% modified codons, more preferably at least 80% modified sequences. As indicated above, the sequences are modified to contain codons having a frequency in maize of at least 20%.

FRTs

The FRT has been identified as a minimal sequence comprising two 13 base pair repeats, separated by an 8 base spacer, as follows (Sequence ID No.: 4):

5'-G A A G T T C C T A T T C[T C T A G A A A]
GTATAGGAACTTC3' wherein the nucleotides within the brackets indicate the spacer region. The nucleotides in the spacer region can be replaced with a combination of nucleotides, so long as the two 13-base repeats are separated by eight nucleotides. FLP is a conservative, site-specific recombinase, capable of catalyzing inversion of a nucleic acid sequence positioned between two inversely oriented FRTs; recombination between two molecules each containing a FRT site; and excision between FRT sites.

The core region is not symmetrical, and its asymmetry dictates the directionality of the reaction. Recombination between inverted FRT sites causes inversion of a DNA sequence between them, whereas recombination between directly oriented sites leads to excision of the DNA between them. Recombination may also occur at a single FRT site, where a template provides matched ends for recombination.

FLP Activity

Assays for FLP recombinase activity are known and generally measure the overall activity of the enzyme on DNA substrates containing FRT sites. In this manner, a frequency of excision of the target sequence can be determined. For example, inversion of a DNA sequence in a circular plasmid containing two inverted FRT sites can be detected as a change in position of restriction enzyme sites. This assay is described in Vetter et al. (1983) *PNAS* 80:7284. Alternatively, excision of DNA from a linear molecule or intermolecular recombination frequency induced by the enzyme may be assayed, as described, for example, in Babineau et al. (1985) *JBC* 260:12313; Meyer-Leon et al. (1987) *NA Res* 15:6469; and Gronostajski et al. (1985) *JBC* 260:12328.

Definitions

"Structural gene" is a DNA sequence that is transcribed into messenger RNA (mRNA) which is then translated into a sequence of amino acids characteristic of a specific polypeptide.

"Expression" refers to the biosynthesis of a gene product. For example, in the case of a structural gene, expression involves transcription of the structural gene into mRNA and the translation of mRNA into one or more polypeptides.

"Expression vector" is a DNA molecule comprising a gene that is expressed in a host cell. Typically, gene expression is placed under the control of certain regulatory elements, including constitutive or inducible promoters, tissue-specific regulatory elements, and enhancers. When the gene is under the control of such regulatory elements the gene is said to be operably linked to the regulatory element.

"Promoter" is a DNA sequence that directs the transcription of a structural gene. Typically, a promoter is located in the 5' prime region of a gene, proximal to the transcription start site of a structural gene.

"Inducible promoter" is a DNA sequence, that upon exposure to an inducing agent, directs that transcription of the associated structural gene.

"Constitutive promoter" is a DNA sequence that directs the transcription of a structural gene in a relatively steady-state manner, e.g. where the rate of transcription is not regulated by an inducing agent.

"Tissue-specific promoter" is a DNA sequence that directs transcription of the associated coding region in a specific tissue type(s) such as leaves, root, or meristem.

"Tissue preferred promoter" is a DNA sequence that directs transcription of the associated coding region at higher levels in specific tissue types such as leaves, root, or meristem.

"Transformed plant cell" A plant cell comprising a DNA region or modification to DNA introduced as a result of the process of transformation "Stably transformed plant" A plant comprising a DNA region or modification to DNA introduced as a result of the process of transformation "Fertile transgenic plant" A plant comprising a DNA region or modification to DNA introduced as a result of the process of transformation "Functional expression of FLP" Production of a FLP site-specific recombinase protein, through proper transcription of the FLP structural gene followed by translation into protein, said protein being capable of binding to FRT recombination target sites and mediating conservative site-specific recombination between FRT target sites.

"FLP" A 423 amino acid protein capable of binding to FRT recombination target sites and mediating conservative site-specific recombination between FRT sites.

"FRT site/sites" The recombination target sites recognized by FLP recombinase protein. The basic configuration consists of a 48 nucleotide DNA sequence consisting of an 8 basepair core and three 13 basepair symmetry elements where two symmetry elements occur in direct orientation on the 5' end of the core sequence and the third element occurs in inverted orientation on the 3' end of the core sequence.

"Transient transfection" Introduction of DNA into cells, where the introduced DNA sequences do not become stably integrated into the genome of the organism but rather persist as non-integrated molecules whose half-life and thus expression are temporally limited based on susceptibility to endogenous nucleic acid or protein degradation cell division processes.

Monocot Plant Cell Transformation

Monocot cells, particularly maize cells, can be transformed to include an FRT nucleic acid sequence or a nucleic acid sequence encoding FLP by known methods for transforming plant cells, as described below.

Gene Transformation Methods

Numerous methods for introducing foreign genes into plants are known and can be used to insert the FLP gene or FRT nucleic acid sequences into a plant host, including biological and physical plant transformation protocols. See, for example, Miki et al., (1993), "Procedure for Introducing Foreign DNA into Plants," In: *Methods in Plant Molecular Biology and Biotechnology*, Glick and Thompson, eds., CRC Press, Inc., Boca Raton, pages 67–88. The methods chosen vary with the host plant, and include chemical transfection methods such as calcium phosphate, microorganism-mediated gene transfer such as Agrobacterium (Horsch, et al. (1985) *Science* 227:1229–31), electroporation, micro-injection, and biolistic bombardment.

Expression cassettes and vectors and in vitro culture methods for plant cell or tissue transformation and regeneration of plants are known and available. See, for example, Gruber, et al., (1993), "Vectors for Plant Transformation" In: *Methods in Plant Molecular Biology and Biotechnology*, Glick and Thompson, eds., CRC Press, Inc., Boca Raton, pages 89–119.

Agrobacterium-Mediated Transformation

The most widely utilized method for introducing an expression vector into plants is based on the natural transformation system of Agrobacterium. *A. tumefaciens* and *A. rhizogenes* are plant pathogenic soil bacteria which genetically transform plant cells. The Ti and Ri plasmids of *A. tumefacients* and *A. rhizogenes*, respectfully, carry genes responsible for genetic transformation of plants. See, for example, Kado, (1991), *Crit. Rev. Plant Sci*. 10:1. Descriptions of the Agrobacterium vector systems and methods for Agrobacterium-mediated gene transfer are provide in Gruber et al., supra; Miki, et al., supra; and Moloney et al. (1989), *Plant Cell Reports* 8:238.

Direct Gene Transfer

Despite the fact that the host range for Agrobacterium-mediated transformation is broad, some major cereal crop species and gymnosperms have generally been recalcitrant to this mode of gene transfer, even though some success has recently been achieved in rice (Hiei et al. (1994) *The Plant Journal* 6:271–282) and maize (Ishida et al. (1996) *Nature/biotechnology* 14:745–750). Several methods of plant transformation, collectively referred to as direct gene transfer, have been developed as an alternative to Agrobacterium-mediated transformation.

A generally applicable method of plant transformation is microprojectile-mediated transformation, where DNA is carried on the surface of microprojectiles measuring about 1 to 4 μm. The DNA generally contained in an expression vector expression vector is introduced into plant tissues with a biolistic device that accelerates the microprojectiles to speeds of 300 to 600 m/s which is sufficient to penetrate the plant cell walls and membranes. (Sanford et al., (1987) *Part. Sci. Technol* 5:27; Sanford (1988) *Trends Biotech* 6:299; Sanford (1990) *Physiol. Plant* 79:206; Klein et al. (1992) *Biotechnology* 10:268).

Another method for physical delivery of DNA to plants is sonication of target cells as described in Zang et al. (1991) *Bio/Technology* 9:996. Alternatively, liposome or spheroplast fusions have been used to introduce expression vectors into plants. See, for example, Deshayes et al. (1985) *EMBO J.* 4:273 1; and Christou et al. (1987) *PNAS USA* 84:3962. Direct uptake of DNA into protoplasts using $CaCl_2$ precipitation, polyvinyl alcohol or poly-L-ornithine have also been reported. See, for example, Hain et al. (1985) *Mol. Gen.Genet.* 199:161; and Draper et al. (1982) *Plant Cell Physiol.* 23:451.

Electroporation of protoplasts and whole cells and tissues has also been described. See, for example, Donn et al. (1990) In: *Abstracts of the VIIth Intl. Congress on Plant Cell and Tissue Culture (IAPTC)* A2–38, page 53; D'Halluin et al. (1992) *Plant Cell* 4:1495–1505; and Spencer et al. (1994) *Plant Mol. Biol.* 24:51–61. Microinjection of DNA into whole plant cells has also been described as has microinjection into protoplasts. See, for example in whole cells, Neuhaus et al. (1987) *Theor. Appl. Genet.* 75:30–36; and in protoplasts, Crossway et al. (1986) *Mol. Gen. Genet.* 202:179–185; and Reich et al. (1986) *Biotechnology* 4:1001–1004.

Particle Wounding/Agrobacterium Delivery

Another useful basic transformation protocol involves a combination of wounding by particle bombardment, followed by use of Agrobacterium for DNA delivery, as described by Bidney et al. (1992) *Plant Mol. Biol.* 18:301–313. Useful plasmids for plant transformation include PHP9762. The binary backbone for PHP9762 is bin 19. See Bevan et al. (1984) *Nucleic Acids Research* 12:8711–8721.

In general, the intact meristem transformation method involves imbibing seed for 24 hours in the dark, removing the cotyledons and root radical, followed by culturing of the meristem explants. Twenty-four hours later, the primary leaves are removed to expose the apical meristem. The explants are placed apical dome side up and bombarded, e.g.) twice with particles, followed by co-cultivation with Agrobacterium. To start the co-cultivation for intact meristems, Agrobacterium is placed on the meristem. After about a 3-day co-cultivation period the meristems are transferred to culture medium with cefotaxime (plus kanamycin for the NPTII selection). Selection can also be done using kanamycin.

The split meristem method involves imbibing seed, breaking of the cotyledons to produce a clean fracture at the plane of the embryonic axis, excising the root tip and then bisecting the explants longitudinally between the primordial leaves. The two halves are placed cut surface up on the medium then bombarded twice with particles, followed by co-cultivation with Agrobacterium. For split meristems, after bombardment, the meristems are placed in an Agrobacterium suspension for 30 minutes. They are then removed from the suspension onto solid culture medium for three day co-cultivation. After this period, the meristems are transferred to fresh medium with cefotaxime (plus kanamycin for selection).

Transfer by Plant Breeding

Once a single transformed plant has been obtained by the foregoing recombinant DNA method, e.g., a plant transformed with a desired gene, conventional plant breeding methods can be used to transfer the structural gene and associated regulatory sequences via crossing and backcrossing. In general, such plant breeding techniques are used to transfer a desired gene into a specific crop plant. In the instant invention, such methods include the further steps of: (1) sexually crossing an FLP transformed plant with a second FRT transformed plant; (2) recovering reproductive material from the progeny of the cross; and (3) growing FLP/FRT-containing plants from the reproductive material.

Preferred FLP/FRT Systems

The FLP/FRT system is used to advantageously excise a gene from a plant genome. For example, a marker gene may be inserted into a maize genome along with a gene of interest. The marker gene is initially useful in demonstrating effective transformation of the plants, but is not desired in the final product. By inducing expression of FLP, preferably moFLP, transiently or from the plant's genome, the unwanted marker gene is excised.

In a preferred method of the invention, a first transgenic plant is produced containing FLP, preferably moFLP, in its genome. A second transgenic plant is produced containing FRT nucleic acid sequences, preferably with a gene positioned between at least one pair of FRTs. By genetically crossing the first and second transgenic plants, a hybrid plant containing both FLP and FRT in the genome is produced. The FLP in the plant genome is preferably under the control of an inducible promoter, such as a heat-inducible promoter or an estradiol-responsive promoter, so that expression of FLP and subsequent excision at the FRT sites is controlled.

Chemical Synthesis of Genes Encoding FLP

The FLP recombinase gene from yeast (*Saccharomyces cerevisiae*) is commercially available in plasmid pOG44 from Stratagene Cloning Systems (11011 North Torrey Pines Road, La Jolla, Calif. 92037).

Once the amino acid sequence of FLP is known, a gene encoding FLP can be synthesized. In addition, the nucleotide sequence of a synthetic gene encoding FLP can be optimized for expression in plants by modifying the codon usage to include plant preferred codons. See, for example, Murray et al. (1989) *NAR* 17: 447. Even more specifically, the nucleotide sequence of a synthetic gene encoding FLP can be optimized for expression in monocotyledonous or dicotyledonous plants. See, for example, Cambell et al. (1990) *Plant Physiol.* 92:1. Genes encoding FLP can be obtained, for example, by synthesizing the genes with mutually priming long oligonucleotides. See, for example, Ausubel et al. (eds.), CURRENT PROTOCOLS IN MOLECULAR BIOLOGY, pages 8.2.8 to 8.2.13 (Wiley Interscience (1990)) ["Ausubel"]. Also, see Wosniak et al. (1987) *Gene* 60:115. Moreover, current techniques using the polymerase chain reaction provide the ability to synthesize genes as large as 1.8 kilobases in length (Adang et al. (1993) *Plant Mol. Biol.* 21:1131; Bombat et al. (1993) *PCR Methods and Applications* 2:266.

Functional fragments of FLP can be identified using a variety of techniques such as restriction analysis, Southern analysis, primer extension analysis, and DNA sequence analysis. Primer extension analysis or S1 nuclease protection analysis, for example, can be used to localize the putative start site of transcription of the cloned gene. Ausubel at pages 4.8.1 to 4.8.5; Walmsley et al. "Quantitative and Qaulitative Analysis of Exogenous Gene Expression by the S1 Nuclease Protection Assay," in METHODS IN MOLECULAR BIOLOGY, VOL. 7: GENE TRANSFER AND EXPRESSION PROTOCOLS, Murray (ed.), pages 271–281 (Humana Press, Inc. 1991). Functional fragments of the FLP protein are identified by their ability, upon introduction to cells containing appropriate FRT substrates, to catalyze site-specific recombination (for example, excision of an FRT-flanked sequence which upon removal will activate an assayable marker gene.

The general approach of such functional analysis involves subcloning DNA fragments of a genomic clone, cDNA clone or synthesized gene sequence into an expression vector, introducing the expression vector into a heterologous host, and screening to detect the product of recombination (i.e. using restriction analysis to verify the product of recombination at the nucleic acid level, or relying on an assay system for recombination as described above). Methods for generating fragments of a cDNA or genomic clone are well known. Variants of an isolated DNA encoding FLP can be produced by deleting, adding and/or substituting nucleotides for the isolated nucleotides, for example, the nucleotide sequence of SEQ ID No: 1 (Table 1). Such variants can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also, see generally, McPherson (ed.), DIRECTED MUTAGENESIS: A Practical approach, (IRL Press, 1991). Thus, the present invention also encompasses DNA molecules comprising nucleotide sequences that have substantial sequence identity with SEQ ID NO: 1 and encode FLP. The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete nucleotide or gene sequence.

(b) As used herein, "comparison window" means includes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wisc., USA; the CLUSTAL program is well described by Higgins and Sharp, *Gene* 73:237–244 (1988); Higgins and Sharp, *CABIOS* 5:151–153 (1989); Corpet, et al., *Nucleic Acids Research* 16:10881–90 (1988); Huang, et al., *Computer Applications in the Biosciences* 8:155–65 (1992), and Person, et al., *Methods of Molecular Biology* 24:307–331 (1994); preferred computer alignment methods also include the BLASTP, BLASTN, and BLASTX algorithms. Altschul, et al., *J. Mol. Biol.* 215:403–410 (1990). Alignment is also often performed by inspection and manual alignment.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. When sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid sequences for these purposes normally means sequence identity of at least 60%, more preferably at least 70%, 80%, 90%, and most preferably at least 95%. Polypeptides which are "substantially similar" share sequences as noted above except that residue positions which are not identical may differ by conservative amino acid changes.

Another indication that nucleotide sequences are substantially identical is if two molecules hybridize to each other under stringent conditions. Generally, stringent conditions are selected to be about 5° C. to about 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, stringent wash conditions are those in which the salt concentration is about 0.02 molar at pH 7 and the temperature is at least about 50, 55, or 60° C. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

Construction of Genes and Vectors

The moFLP nucleotide sequence was derived from a back translation of the protein sequence using maize preferred codons. Sequence analysis was performed using the Wisconsin Sequence Analysis Package from Genetics Computer Group, Madison, Wis. The nucleotide sequence was assembled from a series of synthetic oligonucleotides.

FLP vectors were constructed using standard molecular biology techniques. See, for example, Sambrook et al. (eds.) MOLECULAR CLONING: a LABORATORY MANUAL, Second Edition, (Cold Spring Harbor Laboratory Press, cold Spring Harbor, N.Y. 1989). Plasmids are based on pUC18. The vectors used in these experiments contain combinations of the same basic regulatory elements. The Omega prime (O-) 5-prime sequence is described by Gallie et al. (1987) *Nucl. Acids Res.* 15:3257–3273. The selective marker gene, bar (Thompson et al. (1987) *EMBO J.* 6:2519–2523), was used in conjunction with bailaphos selection to recover transformants. The Cauliflower Mosaic Virus 35S promoter with a duplicated enhancer region is described by Gardner et al. (1981) *Nucl. Acid Res.* 9:2871–2888. The 79 bp Tobacco Mosaic Virus leader is described by Gallie et al. (1987) *Nucl. Acid Res.* 15:3257–3273 and was inserted downstream of the promoter followed by the first intron of the maize alcohol dehydrogenase gene ADH1-S. Described by Dennis et al. (1984) *Nucl. Acid Res.* 12:3983–3990. The 3- sequence pinII is described by An et al. (1989) *Plant Cell* 1: 115–122.

Promoters

A. Inducible Promoters

An inducible promoter is operably linked to a nucleotide sequence encoding FLP. Optionally, the inducible promoter is operably linked to a nucleotide sequence encoding a signal sequence which is operably linked to a nucleotide sequence encoding FLP. With an inducible promoter the rate of transcription increases in response to an inducing agent.

A variety of inducible promoters can be used in the instant invention. See Ward et al. (1993) *Plant Mol. Biol.* 22:361–366. Exemplary inducible promoters include that from the ACE1 system which responds to copper (Mett et al. (1993) *PNAS* 90:4567–4571); In2 gene from maize which responds to benzenesulfonamide herbicide safeners (Hershey et al. (1991) *Mol. Gen. Genetics* 227:229–237 and Gatz et al. (1994) *Mol. Gen. Genetics* 243:32–38) or Tet repressor from Tn10 (Gatz et al. (1991) *Mol. Gen. Genet.* 227:229–237. A particularly preferred inducible promoter is a promoter that responds to an inducing agent to which plants do not normally respond. An exemplary inducible promoter is the inducible promoter from a steroid hormone gene the transcriptional activity of which is induced by a glucocorticosteroid hormone. Schena et al. (1991) *Proc. Natl. Acad. Sci. U.S.A.* 88:10421.

The expression vector comprises an inducible promoter operably linked to a nucleotide sequence encoding FLP. The expression vector is introduced into plant cells and presumptively transformed cells are exposed to an inducer of the inducible promoter. The cells are screened for the presence of FLP protein by introducing an appropriate FRT-containing sequence, that upon excision, promotes expression of a scorable marker such as GUS, GFP, luciferase, or anthocyanin production.

B. Tissue-specific or Tissue Preferred Promoters

A tissue-specific promoter is operably linked to a nucleotide sequence encoding a FLP. Optionally, the tissue-specific promoter is operably linked to a nucleotide sequence encoding a signal sequence that is operably linked to a nucleotide sequence encoding FLP. Plants transformed with a gene encoding FLP operably linked to a tissue-specific promoter produce the FLP protein exclusively, or preferentially, in a specific tissue.

A number of tissue-specific or tissue-preferred promoters can be utilized in the instant invention. Exemplary tissue-specific or tissue-preferred promoters include a root-preferred promoter such as that from the phaseolin gene (Murai et al. (1983) *Science* 23:476–482 and Sengupta-Gopalan et al. (1985) *Proc. Natl. Acad. Sci. USA* 82:3320–3324); a leaf-specific and light-induced promoter such as that from cab or rubisco (Simpson et al. (1985) *EMBO J.* 4(11):2723–2729 and Timko et al. (1985) *Nature* 318:579–582); an anther-specific promoter such as that from LAT52 (Twell et al. (1989) *Mol. Gen. Genet.* 217:240–245); a pollen-specific promoter such as that from Zm13 (Guerrero et al. (1993) *Mol. Gen. Genet.* 224:161–168) or a microspore-preferred promoter such as that from apg (Twell et al. (1993) *Sex. Plant Reprod.* 6:217–224.

The expression vector comprises a tissue-specific or tissue-preferred promoter operably linked to a nucleotide sequence encoding FLP. The expression vector is introduced into plant cells. The cells are screened for the presence of FLP protein by introducing an appropriate FRT-containing sequence, that upon excision, promotes expression of a scorable marker such as GUS, GFP, luciferase, or anthocyanin production.

C. Constitutive Promoters

A constitutive promoter is operably linked to a nucleotide sequence encoding a FLP or the constitutive promoter is operably linked to a nucleotide sequence encoding a signal sequence which is operably linked to a nucleotide sequence encoding FLP.

Many different constitutive promoters can be utilized in the instant invention. Exemplary constitutive promoters include the promoters from plant viruses such as the 35S promoter from CaMV (Odell et al. (1985) *Nature* 313:810–812) and the promoters from such gene as rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730) and maize H3 histone (Lepetit et al. (1992) *Mol. Gen. Genet.* 231:276–285and Atanassova et al. (1992) *Plant Journal* 2(3):291–300).

The ALS promoter, a XbaI/NcoI fragment 5-prime to the *Brassica napus* ALS3 structural gene (or a nucleotide sequence that has substantial sequence similarity to said XbaI/NcoI fragment), represents a particularly useful constitutive promoter. Co-pending Pioneer Hi-Bred International U.S. patent application Ser. No. 08/409,297.

The expression vector comprises a constitutive promoter operably linked to a nucleotide sequence encoding FLP. The expression vector is introduced into plant cells and presumptively transformed cells are screened for the presence of FLP protein by introducing an appropriate FRT-containing sequence, that upon excision, promotes expression of a scorable marker such as GUS, GFP, luciferase, or anthocyanin production.

Foreign Protein Genes and Agronomic Genes

According to the present invention, expression of MoFLP to produce FLP recombinase can be used to modify transgenic sequences that have been previously integrated into the maize genome, through FLP-mediated excision of FRT sequences and the intervening DNA sequence. In such a manner, structural genes whose DNA sequence and/or gene-expression are not desired in the final product can be removed. Thus, marker genes that have utility in the recovery of transgenic events in culture (or during plant growth or reproduction) can be removed from a transgenic event, leaving intact, expressing agronomic expression cassettes in the final product. In the process of excising one sequence, a structural gene can also be moved relative to a promoter to activate the gene (i.e. simply by moving the structural gene next to the promoter, through the removal of transcriptional impediments such as polyA sequences or stop-codons, or through frame shifts).

Depending on the transformation strategy and the desired final product, many of the genes listed below could be candidates for i) marker genes used for recovery of transgenics during transformation that would later be removed from the final commercial product, and also for agronomically important genes to be expressed in the final product (for example, herbicide genes).

In addition, a marker gene for identifying and selecting transformed cells, tissues, or plants should be included in the transformation construct. By marker gene is intended to be either reporter genes or selectable marker genes.

Reporter genes are generally known in the art. The reporter gene used should be exogenous and not expressed endogenously. Ideally the reporter gene will exhibit low background activity and should not interfere with plant biochemical and physiological activities. The products expressed by the reporter gene should be stable and readily detectable. It is important that the reporter gene expression should be able to be assayed by a non-destructive, quantitative, sensitive, easy to perform and inexpensive method.

Examples of suitable reporter genes known in the art can be found in, for example, Jefferson et al. (1991) in *Plant Molecular Biology Manual* (Gelvin et al., eds.) pp. 1–33, Kluwer Academic Publishers; DeWet et al. (1987) *Mol. Cell. Biol.* 7:725–737; Goff et al. (1990) *EMBO J.* 9:2517–2522; Kain et al. (1995) *BioTechniques* 19:650–655; Chiu et al. (1996) *Current Biology* 6:325–330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987–992); methotrexate (Herrera Estrella et al. (1983) *Nature* 303:209–213; Meijer et al. (1991) *Plant Mol. Biol.* 16:807–820); hygromycin (Waldron et al. (1985) *Plant Mol. Biol.* 5:103–108; Zhijian et al. (1995) *Plant Science* 108:219–227); streptomycin (Jones et al. (1987) *Mol. Gen. Genet.* 210:86–91); spectinomycin (Bretagne-Sagnard et al. (1996) *Transgenic Res.* 5:131–137); bleomycin (Hille et al. (1990) *Plant Mol. Biol.* 7:171–176); sulfonamide (Guerineau et al. (1990) *Plant Mol. Bio.* 15:127–136); bromoxynil (Stalker et al. (1988) *Science* 242:419–423); glyphosate (Shaw et al. (1986) *Science* 233:478–481); phosphinothricin (DeBlock et al., (1987) *EMBO J.* 6:2513–2518).

Other genes that could serve utility in the recovery of transgenic events but might not be required in the final product would include, but are not limited to, such examples as GUS (b-glucoronidase; Jefferson (1987) *Plant Mol. Biol. Rep.* 5:387), GFP (green flurescence protein; Chalfie et al. (1994) *Science* 263:802), luciferase (Teeri et al. (1989) *EMBO J* 8:343) and the maize genes encoding for anthocyanin production (Ludwig et al. (1990) *Science* 247:449). For certain applications, for example the commercial production of harvestable protein from transgenic plants as described below, expression of the above genes would be valuable and thus would remain after excision.

Numerous types of genes fall into the category of potentially valuable genes that would remain in the final commercial transgenic event after excision of various unwanted (or simply unnecessary) transgenic elements. Examples are included below;

With transgenic plants according to the present invention, a foreign protein can be produced in commercial quantities. Thus, the selection and propagation techniques described above yield a plurality of transgenic plants which are harvested in a conventional manner, and a foreign protein then is extracted from a tissue of interest or from total biomass. Protein extraction from plant biomass can be accomplished by known methods which are discussed, for example, by Heney et al. (1981) *Anal. Biochem.* 114: 92–6.

According to a preferred embodiment, the transgenic plant provided for commercial production of foreign protein is maize. In another preferred embodiment, the biomass of interest is seed. For the relatively small number of transgenic plants that show higher levels of expression, a genetic map can be generated, primarily via conventional RFLP and PCR analysis, which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269–284 (CRC Press, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR and sequencing, all of which are conventional techniques.

Likewise, by means of the present invention, agronomic genes can be expressed in transformed plants. More particularly, plants can be genetically engineered to express various phenotypes of agronomic interest. The genes implicated in this regard include, but are not limited to, those categorized below including genes that confer resistance to pests or disease and that encode:

plant disease resistance genes (Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al. (1994) *Science* 266:789 (cloning of the tomato Cf-9 gene for resistance to *Cladosporium fulvum*); Martin et al. (1993) *Science* 262:1432 (tomato Pto gene for resistance to *Pseudomonas syringae* pv. tomato encodes a protein kinase); Mindrinos et al. (1994) *Cell* 78:1089 (Arabidopsis RSP2 gene for resistance to *Pseudomonas syringae*).);

*Bacillus thuringiensis* protein, a derivative thereof or a synthetic polypeptide modeled thereon (See, for example, Geiser et al. (1986) *Gene* 48:109, who disclose the cloning and nucleotide sequence of a Bt δ-endotoxin gene. Moreover, DNA molecules encoding δ-endotoxin genes can be purchased from American Type Culture Collection (Rockville, Md.), under ATCC accession Nos. 40098, 67136, 31995 and 31998.);

A lectin (See, for example, the disclosure by Van Damme et al. (1994) *Plant Molec. Biol.* 24:825, who disclose the nucleotide sequences of several *Clivia miniata* mannose-binding lectin genes.);

A vitamin-binding protein such as avidin (See U.S. patent application Ser. No. 07/911,864, the contents of which are hereby incorporated by reference. The application teaches the use of avidin and avidin homologues as larvicides against insect pests.);

An enzyme inhibitor, for example, a protease inhibitor or an amylase inhibitor (See, for example, Abe et al. (1987) *J. Biol. Chem.* 262:16793 (nucleotide sequence of rice cysteine proteinase inhibitor), Huub et aL (1993) *Plant Molec. Biol.* 21:985 (nucleotide sequence of cDNA encoding tobacco proteinase inhibitor I), and Sumitani et al. (1993) *Biosci. Biotech. Biochem.* 57:1243 (nucleotide sequence of *Streptomyces nitrosporeus* α-amylase inhibitor).);

An insect-specific hormone or pheromone such as an ecdysteroid and juvenile hormone, a variant thereof, a mimetic based thereon, or an antagonist or agonist thereof (See, for example, the disclosure by Hammock et al. (1990) *Nature* 344:458, of baculovirus expression of cloned juvenile hormone esterase, and inactivator of juvenile hormone.);

An insect-specific peptide or neuronpeptide which, upon expression, disrupts the physiology of the affected pest (For example, see the disclosures of Regan (1994) *J. Bio. Chem.* 269:9 (expression cloning yields DNA coding for insect diuretic hormone receptor), and Pratt et al. (1989) *Biochem. Biophys. Res. Comm.* 163:1243 (an allostatin is identified in *Diploptera puntata*). See also U.S. Pat. No. 5,266,317 to Tomalski et al., who disclose genes encoding insect-specific, paralytic neurotoxins.); An insect-specific venom produced in nature by a snake, a wasp, etc. (For example, see Pang et al. (1992) *Gene* 116:165, for disclosure of heterologous expression in plants of a gene coding for a scorpion insectotoxic peptide.);

An enzyme responsible for an hyperaccumulation of a monterpene, a sesquiterpene, a steroid, hydroxamic acid, a phenylpropanoid derivative or another non-protein molecule with insecticidal activity;

An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic (See PCT application WO 93/02197 in the name of Scott et al., which discloses the nucleotide sequence of a callase gene. DNA molecules which contain chitinase-encoding sequences can be obtained, for example, from the ATCC under accession Nos. 39637 and 67152. See also Kramer et al. (1993) *Insect Biochem. Molec. Biol.* 23:691, who teach the nucleotide sequence of a cDNA encoding tobacco hookworm chitinase, and Kawalleck et al. (1993) *Plant Molec. Biol.* 21:673, who provide the nucleotide sequence of the parsley ubi4-2 polyubiquitin gene.);

A molecule that stimulates signal transduction (For example, see the disclosure by Botella et al. (1994) *Plant Molec. Biol.* 24:757, of nucleotide sequences for mung bean calmodulin cDNA clones, and Griess et al. (1994) *Plant Physiol.* 104:1467, who provide the nucleotide sequence of a maize calmodulin cDNA clone.);

A hydrophobic moment peptide (See U.S. patent applications Ser. No. 08/168,809 (disclosure of peptide derivatives of Tachyplesin which inhibit fungal plant pathogens) and Ser. No. 08/179,632 (teaches synthetic antimicrobial peptides that confer disease resistance);

A membrane permease, a channel former or a channel blocker. For example, see the disclosure by Jaynes et al. (1993) *Plant Sci.* 89:43, of heterologous expression of a cecropin-β lytic peptide analog to render transgenic tobacco plants resistant to *Pseudomonas solanacearum*.

A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al. (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

An insect-specific antibody or an immunotoxin derived therefrom. Thus, an antibody targeted to a critical metabolic function in the insect gut would inactivate an affected anzyme, killing the insect gut. Cf. Taylor et al., Abstract #497, SEVENTH INT'L SYMPOSIUM ON MOLECULAR PLANT-MICROBE INTERACTIONS (1994) (enzymatic inactivation in transgenic tobacco via production of single-chain antibody fragments).

P. A virus-specific antibody. See, for example, Tavladoraki et al. (1993) *Nature* 366:469, who show that transgenic plants expressing recombinant antibody genes are protected from virus attack.

A developmental-arrestive protein produced in nature by a pathogen or a parasite. Thus, fungal endo α-1,4-D-polygalacturonases facilitate fungal colonization and plant nutrient release by solubilizing plants cell wall homo-α-1, 4-D-galacturonase. See Lamb et al. (1992) *Bio/Technology* 10:1436. The cloning and characterization of a gene which encodes a bean endopolygalacturonase-inhibiting protein is described by Toubart et al. (1992) *Plant J.* 2:367.

R. A developmental-arrestive protein produced in nature by a plant. For example, Logemann et al. (1992) *Bio/Technology* 10:305, have shown that transgenic plants expressing the barley ribosome-inactivating gene have an increased resistance to fungal disease. All of the respective references and the contents thereof are hereby incorporated by reference.

2. Genes That Confer Resistance to a Herbicide, for Example:

A. A herbicide that inhibits the growing point or meristem, such as an imidazalinone or a sulfonylurea. Exemplary genes in this category code for mutant ALS and AHAS enzyme as described, for example, by Lee et al. (1988) *EMBO J.* 7:241, and Miki et al. (1990) *Theor. Appl. Genet.* 80:449, respectively.

B. Glyphosate (resistance imparted by mutant EPSP synthase and aroA genes, respectively) and other phosphono compounds such as glufosinate (PAT and bar genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al. (1989) *Bio/Technology* 7:61, describe the production of transgenic plants that express chimeric bar genes coding for phosphinothricin acetyl transferase activity. Exemplary of genes conferring resistance to phenoxy proprionic acids and cycloshexones, such as sethoxydim and haloxyfop, are the Acc1-S1, Acc1-S2 and Acc1-S3 genes described by Marshall et al. (1992) *Theor. Appl. Genet.* 83:435.

C. A herbicide that inhibits photosynthesis, such as a triazine (psbA and gs+genes) and a benzonitrile (nitrilase gene). Przibilla et al. (1991) Plant Cell 3:169, describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC accession Nos. 53435, 67441 and 67442. Cloning and expression of DNA coding for a glutathione S-transferase is described by Hayes et al. (1992) *Biochem. J.* 285:173.

3. Genes that Confer or Contribute to a Value-Added Trait, Such as:

A. Modified fatty acid metabolism, for example, by transforming a plant with an antisense gene of stearoyl-ACP desaturase to increase stearic acid content of the plant. See Knultzon et al. (1992) *Proc. Natl Acad Sci. USA* 89:2624.

Decreased phytate content

Introduction of a phytase-encoding gene would enhance breakdown of phytate, adding more free phosphate to the transformed plant. For example, see Van Hartingsveldt et al. (1993) *Gene* 127:87, for a disclosure of the nucleotide sequence of an *Aspergillus niger* phytase gene.

A gene could be introduced that reduces phytate content. In maize, this, for example, could be accomplished, by cloning and then re-introducing DNA associated with the single allele which is responsible for maize mutants characterized by low levels of phytic acid. See Raboy et al. (1990) *Maydica* 35:383.

Modified carbohydrate composition effected, for example, by transforming plants with a gene coding for an enzyme that alters the branching pattern of starch. See Shiroza et al. (1988) *J. Bacteriol.* 170:810 (nucleotide sequence of *Streptococcus mutans* fructosyltransferase gene), Steinmetz et al. (1985) *Mol. Gen. Genet.* 200:220 (nucleotide sequence of *Bacillus subtilis* levansucrase gene), Pen et al. (1992) *Bio/Technology* 10: 292 (production of transgenic plants that express *Bacillus licheniformis* α-amylase), Elliot et al. (1993) *Plant Molec. Biol.* 21:515 (nucleotide sequences of tomato invertase genes), Søgaard et al. (1993) *J. Biol. Chem.* 268:22480 (site-directed mutagenesis of barley amylase gene), and Fisher et al. (1993) *Plant Physiol.* 102:1045 (maize endosperm starch branching enzyme II).

EXAMPLES

The invention may be more fully understood with reference to the following examples, which are not intended to limit the scope of the invention.

Example I

FLP MEDIATED RECOMBINATION IN MAIZE CELL CULTURE

The novel gene of the invention, moFLP (Sequence ID NO:1) was prepared by back translation of the protein sequence using maize preferred codons. As shown in the Mze_90.codtable produced by J. Michael Cherry (cherry@frodo.mgh.harvard.edu). Codons for R and P were further optimized for dicot expression R(CGCyAGG), P(CCGyCCC). Codon L was changed from CTG to CTC. At base 703, GCC was changed to GCT. Other changes put stop codons in all five other reading frames.

Sequence analysis was performed using the Wisconsin Sequence Analysis Package from Genetics Computer Group, Madison, Wis. The nucleotide sequence was assembled from a series of synthetic oligonucleotides. Using various vectors and host cells, moFLP was demonstrated as expressing a functional FLP recombinase in maize plant cells.

A. Recombination Intra-Plasmid and Inter-Plasmid

FLP-mediated recombination within a plasmid (intra-plasmid recombination) was measured in BMS cell co-transfected with DNA plasmids expressing FLP (moFLP or FLPy) and plasmids containing FRT sequences. Two FRT sites were contained in plasmid PHP2729. This plasmid includes the first FRT site inserted into the first intron from maize Adh1-S; this sequence was followed, in order, by: the coding sequence of the maize gene C1; the potato gene PinII transcription terminator; and plasmid vector DNA sequence. The second FRT site was positioned after the latter sequence and in the same orientation as the first FRT site. Following this second FRT site was, in order: the portion of the Adh1 gintron sequence that was identical to that portion following the first FRT site; the coding sequence for luciferase; and the PinII transcription terminator. In the absence of FLP-mediated recombination, the PHP2729 plasmid expresses the product of the maize gene, C1, which is one of two classes of transactivators that are both required for expression of the series of structural genes for the biosynthetic pathway of anthocyanin, a red pigment. In the presence of FLP-mediated recombination, expression of C1 is turned off and expression of luciferase is turned on. Thus, luciferase activity in cells containing the PHP2729 plasmid indicates recombination between the two FRT sites due to FLP recombinase activity.

It is noted that luciferase expression did not have to depend wholly on intra-plasmid recombination, since multiple copies of the plasmid could have been introduced into each cell after bombardment. Such multiple copies could have permitted inter-plasmid recombination between the plasmids resulting in a functional luciferase expression unit. However, luciferase activity does indicate the presence of FLP recombinase activity.

FLP-mediated recombination between plasmids (inter-plasmid recombination) was measured in BMS cells co-transfected with plasmids PHP2182 and PHP2183. Each of these two plasmids contains a single FRT site. Upon FLP-mediated recombination between the FRT sites, a functional luciferase expression unit is created.

Cell Culture

Yeast FRT recombinase sites (FRT-1) were evaluated as substrates for FLP recombinase activity in BMS cells (genotype Black Mexican Sweet). The cells were obtained from Dr. David Somers (see Kaeppler, et al., (1990), *Plant Cell Reports* 9:415–418), University of Minnesota, and grown in liquid suspension medium. The medium included 4.3 g/l MS salts, 0.5 mg/l thiamine-HCl, 150 mg/l L-asparagine, 2 mg/l 2, dichlorophenoxyacetic acid (2,4-D), 20 g/l sucrose, pH 5.8. Cells were incubated at 27° C. on a rotary platform shaker at approximately 100 rpm in the dark. Cells were subcultured every seven days for maintenance, by transferring 10 ml of suspension into 50 ml of fresh medium.

DNA Particle Bombardment

Cells were resuspended in fresh medium one day prior to bombardment and incubated as described above. On the day of bombardment, cells were resuspended in osmoticum (MS basal medium, Musashige and Skoog (1962) *Physiol. Plant* 15:473–497, with 0.25 M sorbitol), at 25 mg cells/ml for a total volume of 60 ml, and incubated as described above for an additional three hours. One ml of cell-suspension (containing about 25 mg cells) was distributed evenly into petri dishes (60 mm diameter×20 mm height) containing two paper filter disks (Baxter S/P #363, 5.5 cm diameter), prewetted with one ml osmoticum, onto the top filter. The cells on the filter were used as the bombardment target.

For particle bombardment, plasmid DNA (described below) was precipitated onto 1.8 $\mu$m tungsten particles using standard $CaCl_2$-spermidine chemistry (see, for example, Klein et al. (1987) *Nature* 327:70–73). Each plate was bombarded once, using a DuPont Helium Gun (Lowe et al. (1995) *Bio/Technol* 13:677–682). After bombardment, an additional 0.5 ml of osmoticum was added to each plate. All plates were incubated in the dark at 27° C. for two days, after which crude extracts were prepared and assayed for luciferase activity and total cell protein.

The plasmids used in this study were designed to demonstrate functional FLP recombinase activity and FRT recombination in maize cells through transient transgene expression, driving the reaction entirely with plasmid-borne templates. Plasmids used in these studies included those shown below in Tables I-A-1 and I-A-2:

For features of plasmid DNAs for expressing FLP protein:

TABLE I-A-1

| PHP | Promoter | Other 5' Elements | Structural Gene | 3' Elements |
|---|---|---|---|---|
| 4894 | Enhanced CaMV35S | Omega'/Adh-1 intron | MoFLP | PinII terminator |
| 5095 | Ubi-1 | Ubi-1 exon 1 Ubi-1 intron 1 | FLPy | PinII terminator |
| 5096 | Ubi-1 | Ubi-1 exon1 Ubi-1 intron1 | MoFLP | PinII terminator |

For features of plasmid DNAs containing FRT(s):

TABLE I-A-2

| PHP | Promoter | Other 5' Elements | Structural Gene | 3' Elements | Note |
|---|---|---|---|---|---|
| 2175 | Enhanced CaMV35S | omega'/Adh1 intron, with FRT site inserted into Adh1 intron | Luciferase | PinII Terminator | Positive control for PHP2729 and for combination of PHP2182 + PHP2183 |
| 2182 | No promoter | FRT/(3' portion of Adh1 intron) | Luciferase | PinII Terminator | Does not express Luciferase; if correctly recombined with PHP2183, reconstitutes functional expression unit |
| 2183 | Enhanced CaMV35S | omega'/Adh1 intron, with FRT site inserted into Adh1 intron | GUS | PinII terminator | See Comment for PHP2182 above |
| 2729 (first group of elements) | Enhanced CaMV35s | omega'/Adh1 intron, with FRT site inserted into Adh1 intron | C1 | PinII Terminator | In absence of FLP mediated recombination, expresses C1 but not Luciferase; with FLP protein mediated recombination between |

TABLE I-A-2-continued

| PHP | Promoter | Other 5' Elements | Structural Gene | 3' Elements | Note |
|---|---|---|---|---|---|
| 2729 (second group of elements) | No promoter | FRT/(3' portion of Adh1 intron) | Luciferase | PinII Terminator | FRT sites, expresses Luciferase not C1 same orientation as first group, downstream (3') of first group, and separated by intervening vector sequence. |

Cells were bombarded with particular combinations of plasmids to achieve the experimental designs shown below in Table I-A-3.

For an experimental design:

TABLE I-A-3

| Treatment # | PHP2729 FRT | PHP5095 FLPy | PHP5096 MoFLP | PHP2182 ---F | PHP2183 RT--- | PHP4894 MoFLP | PHP2175 FRT | Note |
|---|---|---|---|---|---|---|---|---|
| 1 | 5 µg | 1 µg | | | | | | assay for |
| 2 | 5 µg | | 1 µg | | | | | intra-plasmid |
| 3 | 5 µg | | 0.2 µg | | | | | recombination |
| 4 | 5 µg | | 0.04 µg | | | | | |
| 5 | 5 µg | | | | | | | |
| 6 | | | | 3 µg | 3 µg | | | assay for |
| 7 | | | | 3 µg | 3 µg | 0.04 µg | | inter-plasmid |
| 8 | | | | 3 µg | 3 µg | 0.2 µg | | recombination |
| 9 | | | | 3 µg | 3 µg | 1 µg | | control |
| 10 | | | | | | | 0.01 µg | positive |
| 11 | | | | | | | 0.1 µg | controls for |
| 12 | | | | | | | 1.0 µg | treatments |
| 13 | | | | | | | 5.0 µg | #1–9 above |

Luciferase Assay

Two days after particle bombardment, cells were examined for C1 activity (red pigment) and assayed for luciferase activity. For the luciferase assay, cells were scraped from the filter paper of each plate, transferred to a 1.5 mm Kontes microfuge tube and lysed by grinding in 200 µl lysis buffer (40 mM sodium phosphate, pH 6.8, 1 mM EDTA, 50 mM β-mercaptoethenol) while keeping cool on ice. All samples were centrifuged at 4000×g, 15 minutes at 4° C. and kept on ice. A volume of 20 µl of each extract was added to 200 µl of room temperature luciferase assay buffer (25 mM tricine, pH 7.8, 15 mM $MgCl_2$, 5 mM ATP, 500 µg/ml BSA) in a cuvette. The cuvette was immediately placed into an Analytical Luminescence Laboratories Monolight 2010 Luminometer with automatic injection of 100 µl of 0.5 mM D-luciferin (potassium salt) to start the luminescence action. The device collected relative light units (R.L.U.) for a duration of 10 seconds.

Duplicate reactions for each of the samples described above were set up in separate wells of flat-bottom transparent microtitre plates, by adding 159 microliters of water, one microliter of crude extract and, lastly, 40 microliters BioRad Laboratories Bradford Dye Concentrate, and then mixing by repeated pipetting. After 5 to 45 minutes, the optical density at 595 nm was measured with a micro plate spectrophotometer. The amount of protein present was estimated using a standard curve of BSA protein.

Recombination Between Plasmids Inter-plasmid and Recombination moFLP produced active FLP protein, promoting intra-plasmid and inter-plasmid recombination. As shown in data table I-A-4 below (treatments 6–9), plasmid PHP4894 containing moFLP expressed sufficient FLP recombinase to promote the necessary inter-plasmid recombination required for reconstitution of a functional expression unit for luciferase from plasmids PHP2182 and PHP2183.

Also shown below in data table I-A-4 (treatments 1–5), both FLPy and moFLP produce active LP protein, promoting intra-plasmid recombination. Recombinase activity expressed in luciferase units appeared to be higher from moFLP (treatments 2–4), as compared with FLPy (treatment 1).

TABLE I-A-4

| | Luciferase Activity (R.L.U./µg total protein) | | |
|---|---|---|---|
| Treatment # | Mean | Standard Deviation | Mean %** templates recombined |
| 1 | 667 | 187 | 16% |
| 2 | 776 | 216 | 20% |
| 3 | 1301 | 254 | 26% |
| 4 | 1026 | 107 | 22% |
| 5 | 4.9 | 4.2 | 2.2% |
| 6 | 3.5 | 0.8 | 2.7% |
| 7 | 93.7 | 51.9 | 12.7% |
| 8 | 107.4 | 55.9 | 13.3% |
| 9 | 182.8 | 24 | 17.3% |
| 10 | 0.7 | 1.0 | — |
| 11 | 3.5 | 3.2 | — |
| 12 | 759 | 481 | — |
| 13 | 14916 | 9665 | — |

*n = 3
**based on standard curve of dose response series of the positive control, PHP2175

B. Confirmation of FLP-Mediated Recombination

The FLP-mediated intra-plasmid and inter-plasmid recombination studies described above for Example IA were repeated, and as shown in Table I-B-1, confirmed the increase FLP recombinase activity of moFLP (treatments 2–4) over FLPy (treatment 1).

TABLE I-B-1

| | Luciferase Activity (R.L.U./μg total protein)* | | |
|---|---|---|---|
| Treatment # | Mean Luciferase | Standard Deviation | Mean % templates recombined, |
| 1 | 290.2 | 189.9 | 31.4% |
| 2 | 399.9 | 228.2 | 47.0% |
| 3 | 348.6 | 48.1 | 39.2% |
| 4 | 463 | 143 | 49.7% |
| 5 | 22.0** | 22.1** | 1.0%** |
| 6 | 4.0 | 1.1 | 0.2% |
| 7 | 31.3 | 17.0 | 0.82% |
| 8 | 23.9 | 7.4 | 0.82% |
| 9 | 18.5 | 5.6 | 0.75% |
| 10 | 2.6 | 10.5 | |
| 11 | 49.6 | 34.3 | |
| 12 | 228.5 | 33.8 | |
| 13 | 1387.8 | 288.7 | |
| 14 | −0.6 | 0.8 | |

*n = 3
**n = 2

C. moFLP is More Active at Lower Doses

Transient expression and dose responsive FLP recombinase activity of FLPy versus moFLP was assessed using the FRT and FLP plasmids described above and using the methods described for Example IA. Specifically, varying amounts of FRT and FLP-expresing plasmids were used, as shown below in experimental design table I-C-1. To mantain a constant level of 35S promoter-containing plasmids, control plamid PHP611 was added as required. This plasmid contains the BAR structural gene driven by the Enhanced CaMV35S promoter.

and calculation and expression of the data were performed as described above for Example IA. As shown below in data table I-C-2, the moFLP DNA coding sequence in plasmid PHP5096 (treatments 5–8, 10) conferred higher rates of expression by means of increased efficiency of translation, as compared to the FLPy sequence in PHP5095 (treatments 1–4, 9). This trend is suggested by recombination events using both types of plasmid template series, PHP2729 for intra-plasmid recombination (treatments 1–8) and plasmids PHP2182 and PHP2183 for inter-plasmid recombination (treatments 9–10).

TABLE I-C-2

| | | | Luciferase Activity (R.L.U./μg total protein) | |
|---|---|---|---|---|
| | Treatment # | | Mean | Standard Deviation |
| FLPy | 1 | 1.0 | 56.0 | 22.3 |
| | 2 | 0.02 | 12.6 | 4.1 |
| | 3 | 0.004 | 14.2 | 12.5 |
| | 4 | 0.0008 | 13.5 | 2.3 |
| moFLP | 5 | 0.1 | 190.1 | 15.3 |
| | 6 | 0.02 | 203.8 | 83.8 |
| | 7 | 0.004 | 105.7 | 27.2 |
| | 8 | 0.0008 | 15.6 | 5.5 |
| FLPy | 9 | 0.02 | 30.1 | 5.4 |
| moFLP | 10 | 0.02 | 88.0 | 24.6 |
| CTR | 11 | | 0.3 | 0.1 |
| CTR | 12 | | 11.4 | 3.7 |
| CTR | 13 | | 1058 | 347 |
| CTR | 14 | | 3249 | 603 |
| CTR | 15 | | 10.0 | 7.0 |
| CTR | 16 | | 25.3 | 4.2 |

The data tables shown above demonstrate the gene of the invention, moFLP produced more recombinase activity in maize cells than did FLPy for both intra-plasmid recombination and inter-plasmid recombination.

D. Dose Response FLP

Reinforcing the results in Example I-C, moFLP produces higher recombination frequency at lower plasmid levels,

TABLE I-C-1

Table Describing Combination of Mass and Type of Input Plasmid DNAs

| Treatment # | PHP2729 FRT | PHP5095 FLPy | PHP5096 MoFLP | PHP2182 FRT | PHP2183 FRT | PHP4894 Control | PHP2175 Control |
|---|---|---|---|---|---|---|---|
| 1 | 5 μg | 1 μg | | | | | |
| 2 | 5 μg | 0.02 μg | | | | | |
| 3 | 5 μg | 0.004 μg | | | | | |
| 4 | 5 μg | 0.0008 μg | | | | | |
| 5 | 5 μg | | 0.1 μg | | | | |
| 6 | 5 μg | | 0.02 μg | | | | |
| 7 | 5 μg | | 0.004 μg | | | | |
| 8 | 5 μg | | 0.0008 μg | | | | |
| 9 | | 0.02 μg | | 5 μg | 5 μg | | |
| 10 | | | 0.02 μg | 5 μg | 5 μg | | |
| 11 | | | | | | 0.01 μg | 10 μg |
| 12 | | | | | | 0.1 μg | 9.9 μg |
| 13 | | | | | | 1 μg | 9 μg |
| 14 | | | | | | 10 μg | |
| 15 | 5 μg | | | | | | |
| 16 | | | | 5 μg | 5 μg | | |

Cells were cultured and prepared for bombardment, as described above for Example IA. Appropriate amounts of plasmid DNA, as shown in Table I-C-1, were used to coat particles and bombard the cells as described above for Example IA. Assay of luciferase activity and total protein compared to FLPy (when substrates are co-delivered with the FLP expression plasmid). The FLP dose response study of Example I-C comparing FLPy and moFLP was repeated and expanded using higher amounts of FLPy, as shown below in the experimental design table, Table I-D-1.

TABLE I-D-1

| Treatment # | PHP2729 FRT | PHP5095 FLPy | PHP5096 moFLP | PHP2182 FRT | PHP2183 FRT | PHP4894 Control | PHP2175 Control |
|---|---|---|---|---|---|---|---|
| 1 | 5 μg | 2.5 μg | | | | | |
| 2 | 5 μg | 0.5 μg | | | | | |
| 3 | 5 μg | 0.1 μg | | | | | |
| 4 | 5 μg | 0.02 μg | | | | | |
| 5 | 5 μg | | 0.1 μg | | | | |
| 6 | 5 μg | | 0.02 μg | | | | |
| 7 | 5 μg | | 0.004 μg | | | | |
| 8 | 5 μg | | 0.0008 μg | | | | |
| 9 | | 0.02 μg | | 5 μg | 5 μg | | |
| 10 | | | 0.02 μg | 5 μg | 5 μg | | |
| 11 | | | | | | 5.0 μg | 5.0 μg |
| 12 | | | | | | 1.0 μg | 9.0 μg |
| 13 | | | | | | 0.1 μg | 9.9 μg |
| 14 | | | | | | 0.01 μg | 10.0 μg |
| 15 | 5 μg | | | | | | |
| 16 | | | | 5 μg | 5 μg | | |

Cells were incubated and bombarded with plasmid DNA, as described above for Example 1A. Luciferase activity and total protein was assayed and calculated, as described above. As shown below in data table I-D-2, trends observed in the earlier experiments for recombination of FRT-containing plasmid DNA's co-delivered with plasmids coding for FLP expression were continued. Use of the plasmid containing moFLP produced more recombinase activity than FLPy for intra-/inter-plasmid recombination using PHP2729 as substrate (treatments 1–4=FLPy; treatments 5–8=moFLP). Plasmids containing moFLP of the invention also demonstrated expression of higher recombinase activity mediating inter-plasmid recombination than that expressed from FLPy plasmids when PHP2182 and PHP2 183 were co-delivered to cells as substrates (treatments 9 and 10). The efficiency of expression was based on linear portions of dose response curves for PHP5095 and PHP5096.

TABLE I-D-2

| | Treatment # | | Luciferase Activity (R.L.U./μg total protein)* | | Mean % Templates recombined* |
|---|---|---|---|---|---|
| | | | Mean Luciferase Activity | Standard Deviation | |
| FLPy | 1 | 2.5 μg | 5756 | 3240 | 23.50% |
| | 2** | 0.5 μg | 567 | 265 | 9.93% |
| | 3 | 0.1 μg | 146.2 | 38.2 | 1.05% |
| | 4 | 0.02 μg | 132.6 | 30.9 | 0.92% |
| moFLP | 5 | 0.1 μg | 2372 | 766 | 23.50% |
| | 6 | 0.02 μg | 1547 | 403 | 5.20% |
| | 7 | 0.004 μg | 1735 | 377 | 9.20% |
| | 8 | 0.008 μg | 362 | 82 | 2.60% |
| FLPy | 9 | 0.02 μg | 69.5 | 35.7 | 0.28% |
| moFLP | 10 | 0.02 μg | 443.4 | 174.7 | 1.6% |
| Control | 11 | | 29480 | 4402 | |
| Control | 12 | | 6727 | 2986 | |
| Control | 13 | | 451.4 | 26.8 | |
| Control | 14 | | 35.9 | 3.8 | |
| Control | 15 | | 21.5 | 2.0 | |
| Control | 16 | | 26.9 | 8.6 | |

*n = 3 based on standard curve of dose response series of the positive control, PHP2175
**n = 2

E. Evaluation of FRT and FLP Constructs in an Embryogenic Callus

In Embryogenic maize callus, the efficiency of moFLP was about 35 fold that of FLPy. The transient expression assays described above for assessment of the efficiency of plasmids expressing moFLP and FLPy were repeated using maize embryogenic callus obtained from #3-44-6E1, similar to the culture described in Ludwig, et al., (1990), Science 247:449–50. #3-44-6E1 is a cross between female parent (wx5-9, w23) and male parent (HD2233 A63). To prepare the cell suspension, immature embryos (approximately 1.5 mm in length) were harvested from ears approximately 10–12 days after pollination. The embryos were placed axis down (scutellum up) on culture initiation medium. For example, a typical culture initiation medium contains N6 salts, Erikkson's vitamins, 0.69 g/l proline, 2 mg/l 2,4-D and 3% sucrose. Friable callus initiates from the scutellum and is subcultured periodically onto fresh medium. Friable callus is then placed into liquid medium on a rotary shaker, using well-established methods for subcuturing and maintenance of the resulting suspension culture. For an example of standard media and methods for initiation, maintenance of friable, type II callus and suspension cultures see Sellmer et al., (1994), In "The Maize Handbook", M. Freeling and V. Walbot, eds. Springer-Verlag, New York, pp 671–684.

The cell suspension was routinely maintained in liquid medium (4.3 g MS salts/l, 0.1 g myo-inositol/l, 0.5 mg/l/ nicotenic acid, 0.02 mg/l thiamine-HCl, 0.5 mg/l pyrodoxine-HCl, 2 mg/l L-lysine, 2 mg/l 2, 4-D, 30 g sucrose/l, final pH 5.6) in the dark at 27° C. on a rotary platform shaker at about 100 rpm, and at 1–3 gram cell weight/60 ml medium.

Cells were resuspended in fresh medium on the day prior to bombardment. Two hours prior to bombardment, cells were resuspended at 1.5 gram wet weight per 60 ml osmoticum and incubated. After the incubation, one ml aliquots of cell suspension were pipetted onto pre-wetted paper filter discs in petri dishes, as described above for Example I-A.

Particle bombardment was carried out using the FRT and FLP-containing plasmids and methods described above for Examples IA–ID. Control plasmid PHP610 (Enhanced CaMV35s::AdhI intron::bar::pinII) expressing the bar gene was used as an indicator of bombardment efficiency. After bombardment, additional osmoticum (0.25–0.5 ml) was added to each plate and the plates then incubated in the dark at 27° C. for one day. The cells were then harvested, crude extracts prepared, and samples assayed for luciferase activity and total cell protein as described above. The experimental design is shown in table I-E-1 below:

TABLE I-E-1

| Treatment # | PHP2729 FRT | PHP610 Control | PHP5095 FLPy | PHP5096 moFLP | PHP2175 FRT |
|---|---|---|---|---|---|
| 1 | 5 μg | 5 μg | | | |
| 2 | 5 μg | 2.5 μg | 0.02 μg | | |
| 3 | 5 μg | 2.4 μg | 0.1 μg | | |
| 4 | 5 μg | 2.0 μg | 0.5 μg | | |
| 5 | 5 μg | | 2.5 μg | | |
| 6 | 5 μg | 2.5 μg | | 0.0008 μg | |
| 7 | 5 μg | 2.5 μg | | 0.004 μg | |
| 8 | 5 μg | 2.5 μg | | 0.02 μg | |
| 9 | 5 μg | 2.4 μg | | 0.1 μg | |
| 10 | | 10 μg | | | 0.01 μg |
| 11 | | 9.9 μg | | | 0.1 μg |
| 12 | | 9.0 μg | | | 1.0 μg |
| 13 | | 5.0 μg | | | 5.0 μg |

The cells were bombarded, incubated, and tested for luciferase activity and total protein, as described above. The data, shown below in Table I-E-2 indicates the same trends observed using BMS cells. The plasmid expressing maize-optimized moFLP (treatments 6–9) was more efficient in expressed FLP recombinase activity than the plasmid expressing FLPy (treatments 2–5). The efficiency of moFLP was about 35 fold that of FLPy in this experiment.

TABLE I-E-2

| | Luciferase Activity (R.L.U./μg total protein)* | |
|---|---|---|
| Treatment # | Mean | Standard Deviation |
| 1 Control | 5.4 | 2.9 |
| 2 FLPy | 114.3 | 52.9 |
| 3 | 245.3 | 105.5 |
| 4 | 808.5 | 223.4 |
| 5 | 1248.9 | 322.9 |
| 6 moFLP | 113.3 | 115.8 |
| 7 | 315.7 | 106.3 |
| 8 | 446.2 | 297.9 |
| 9 | 295.2 | 231.3 |
| 10 Control | 2.8 | 1.6 |
| 11 | 23.5 | 10.6 |
| 12 | 194 | 275.4 |
| 13 | 742.9 | 463.5 |

*n = 3

F. Ubi and CaMV35S Promoters for Expression of FLP

Ubi-driven moFLP expression produced higher levels of FLP-mediated excision than the Enhanced CaMV35S promoter, and the addition of FRT to the FLP coding sequence did not abolish activity of the FLP. The expression of moFLP under the control of the Ubiquetin (Ubi) and the 35S Cauliflower Mosaic Virus (CaMV 35S) promoters was compared. In addition, expression of moFLP having an FRT site at the N-terminus of its coding sequence was evaluated. The specific plasmids used are described below in Table I-F-1.

For features of plasmid DNAs for expressing FLP protein:

TABLE I-F-1

| Plasmid PHP | Promoter | Other 5' Elements | Structural Gene | 3' Elements | Note |
|---|---|---|---|---|---|
| 5849 | Enhanced CaMV 35S | omega'; Adh1 intron I; FRT | moFLP | PinII | If FRT does not interfere with FLP expression, then, when moFLP is excised another structural gene will be moved adjacent to the CaMV promoter, activating this second gene |
| 3456 | Enhanced CaMV 35S | omega'; Adh1 intron I; ATG codon; FRT; ~1.8 KB Adh1 intervening sequence; FRT | GUS | PinII | GUS(−) until FLP-mediated excision of intervening 1.8 KB AdhI sequence |
| 3457 | Enhanced CaMV 35S | omega'; 5' portion of Adh1 Intron I; ATG codon; FRT | GUS | PinII | GUS(+) the expected product after excision in PHP3456 |
| 5401 | Ubi-1 | Ubi-1 exon 1 + intron 1; ATG codon; FRT; ~1.8 KBAdhI sequence; FRT | GUS | PinII | GUS(−) until FLP-mediated excision of intervening 1.8 KB AdhI sequence |

The experimental design is shown below in Table I-F-2:

TABLE I-F-2

| Treatment # | PHP5096 Ubi-moFLP | PHP3456 CaMV FRT | PHP5849 CaMV FRT/moFLP | PHP5401 Ubi-FRT | PHP3457 GUS Control | PHP610 Control |
|---|---|---|---|---|---|---|
| 1 | | | | | | |
| 2 | | 10 μg | | | | |
| 3 | | 10 μg | 0.004 μg | | | |
| 4 | | 10 μg | 0.02 μg | | | |
| 5 | | 10 μg | 0.1 μg | | | |
| 6 | | 10 μg | 0.5 μg | | | |
| 7 | 0.0008 μg | 10 μg | | | | |
| 8 | 0.004 μg | 10 μg | | | | |
| 9 | 0.02 μg | 10 μg | | | | |
| 10 | 0.1 μg | 10 μg | | | | |
| 11 | 0.0008 μg | | | 10 μg | | |
| 12 | 0.004 μg | | | 10 μg | | |
| 13 | 0.02 μg | | | 10 μg | | |
| 14 | 0.1 μg | | | 10 μg | | |

TABLE I-F-2-continued

| Treatment # | PHP5096 Ubi- moFLP | PHP3456 CaMV FRT | PHP5849 CaMV FRT/moFLP | PHP5401 Ubi- FRT | PHP3457 GUS Control | PHP610 Control |
|---|---|---|---|---|---|---|
| 19 | | | | | 0.01 μg | 10 μg |
| 20 | | | | | 0.1 μg | 9.9 μg |
| 21 | | | | | 1.0 μg | 9.0 μg |
| 22 | | | | | 10 μg | |
| 24 | | | | 10 μg | | |

Culture conditions, DNA particle bombardment and assays were performed as described above for Examples IA–IE. GUS fluorescence assay was performed as described in Rao and Flynn (1990) *Biotechnique* 8:38–40.

As shown below in Data Table 1-F-3, FRT-containing plasmids were silent for transient expression of reporter GUS in the absence of co-delivered FLP expression vector (treatments 1–2), but were activated to expression levels 100–1000 fold over that of background in the presence of co-delivered FLP. Addition of FRT to the FLP coding sequence in PHP5849 did not abolish activity of the FLP (treatments 3–6). Use of the Ubi promoter resulted in greater FLP-mediated excision activity than previously seen with the CaMV35S promoter.

TABLE I-F-3

| | GUS Fluorescent Units/ μg total protein | |
|---|---|---|
| Treatment # (n = 3) | Mean | Standard Deviation |
| 1 | 1.46 | 0.29 |
| 2 | 1.90 | 0.70 |
| 3 | 6.43 | 4.47 |
| 4 | 49.9 | 6.0 |
| 5 | 254 | 71.1 |
| 6 | 279 | 27.7 |
| 7 | 72.3 | 12.2 |
| 8 | 216 | 79.6 |
| 9 | 391 | 95.0 |
| 10 | 465 | 186 |
| 11 | 572 | 168 |
| 12 | 888 | 264 |
| 13 | 2216 | 268 |
| 14 | 4622 | 1175 |
| 15 | 2.21 | 7.77 |
| 16 | 15.12 | 17.63 |
| 17 | 49.2 | 14.8 |
| 18 | 564 | 144 |
| 19 | 7.65 | 7.23 |

Example II

FLP MEDIATTED EXCISION IN MAIZE CELLS

Transient expression of moFLP will excise an FRT-delimited sequence from the genome of maize cells. Transgenic maize cell lines containing FRT sites integrated into the genome were produced as described below. These cells were then used to evaluate FLP-mediated excidion of FRT-flanked integrated DNA sequences.

A. Intergration of FRT Sites in Maize Genome

BMS cells were obtained from Dr. Somers, as described above. Cells were incubated and maintained as describie above in Example I, for culture of BMS cells in medium 237.

To produce transformed cells containing integrated FRT sequences, the FRT-containing plasmid PHP5401 (described above for Example I-F, Table I-F-1) and the control, ALS #2-containing plasmid PHP2545 containing the maize ALS#2 structural gene conferring GLEAN® resistance driven by the Enhanced CaMV35S promoter with the Omega' element, the Adh1 gintron I and the nos 3' element) were used. Cells transformed with PHP5401 express GUS upon FLP-mediated excision of a 1.8 kb Adh-1 sequence from between the plasmid's FRT sequences. Cells transformed with the control PHP2545 express the maize gene ALS#2, which confers resistance to GLEAN® (Dupont, Inc.). GLEAN® resistance was used to screen for transformed cells.

Cells co-transformed with the FRT-containing plasmid PHP5601 and the ALS#2-containing plasmid PHP2545 were initially screened for GLEAN® resistance. For each plate of cells after bombardment, the top filter with cells was transferred to a plate of #306 medium (4.3 g MS salts/L, 0.1 g myo-inositol/L, 2 mg/l L-glycine, 1 mg/L 2,4-D, 30 g/L sucrose, 3 g/l Gelrite, final pH=5.6). The cells were incubated at 27° C. in the absence of light, for 3 days. The cells were then resuspended in 4 ml #237 medium and pipetted into 4 plates of #306 N medium (#306 medium plus 20 ppb GLEAN®) at 1 ml cell suspension/plate. Independent transformants were subcultured to separate plates of #306N as they appeared over the next 6–8 weeks. GLEAN®-resistant transformants were obtained and used to assay for FRT transformants using transient expression of FLP as described more fully below.

B. Screening for FRT Sequences Using FLP

The GLEAN®-resistant transformants produced as described above, were screened by transient FLP expression, for co-transformants carrying integrated FRT-containing transgenic plasmid DNA sequences. In summary, transformed cells were bombarded with DNA particles containing an FLP-expressing plasmid (PHP5096, as described for Example I, Table I-A-1). The experimental design is shown below in Table II-B-1. The positive control FRT-containing PHP5401 is described in Example I, Table I-F-1. The negative Control PHP687 containing anthocyanin genes C1 and R (Ludwig, et al., (1990), *Science* 247:449–451). This plasmid, PHP687, contained two structural genes, R and C1, each driven by Enhanced CaMV35S, with the Omega' element and the Adh1 intron I, and followed by the 3' pinII sequence. The bombardment protocol was that described above for Example I. Cells were then screened for GUS expression, indicative of FLP-mediated excision events.

TABLE II-B-1

| Treatment # | Cells | Total number of plates shot, 5 trfs/plate | PHP5096 (moFLP) | PHP687 (CI Control) | PHP5401 (FRT) | Note |
|---|---|---|---|---|---|---|
| 1 | GLEAN ®-Resistant transformants treatment #1 (N = 66) | 14 | 1 µg | 0.5 µg | | |
| 2 | BMS Control Cells | 3 | 1 µg | 0.5 µg | | Negative control-expect Cl and no GUS+ |
| 3 | BMS Control | 3 | 1 µg | 0.5 µg | 8 µg | Positive control for FLP expression- +GUS assay, +Cl |

Following bombardment, fresh medium was added to samples, which were incubated for two days at 27° C. in the dark. Cells were assayed for expression of C1 (red cells) versus GUS (blue cells). In the GUS assay, after another day of incubation, the bottom filters on each petri dish were replaced with dry ones, and 1 ml X-Gluc stain (50 mm $NaPO_4$, pH 7.0, 0.1% X-Gluc, 0.1% Triton X100 0.1% sarkosyl, 1.25% DMSO) was added to each plate. Samples were then examined for blue-staining foci, (GUS+) indicative of FLP expression and activity at FRT sites in BMS-FRT cells.

The results are shown below in Table II-B-2. At least two events were positive for carrying transgenic FRT DNA sequences accessible to FLP expressed transiently.

TABLE II-B-2

| Treatment # | Sample size (n) | Red cell counts (transfection efficiency - C1) | Events producing blue cells (GUS+) | Note |
|---|---|---|---|---|
| 1 GLEAN ® resistant BMS-FRT | 66 | Ranged from <10 to >400 per transformant | Event # "1A-14" [1 blue cell] [>100 red cells]; Event # "1B-12" [131 foci] [~50 red cells] | Nearly all foci appeared to be restricted to one cell; not as intense as observed in treatment #3 below. |
| 2 Negative Control | 3 | >100 | None | |
| 3 Positive Control | 3 | >100 | >100 | Foci heterogeneous in staining intensity (many very intense, wide, as usually observed in past) |

C. FLP Activation of Genomic FRT Sites

Transcormed maize cells carrying integrated FRT sites prepared for Example II-A (transformants -1 and -2) were maintained on #306N medium. To confirm FLP-mediated activation of integrated FRT sites in FRT-transformed cells, the FLP-transient expression assay of Example II-B was repeated, using a control plasmid to monitor DNA delivery. The experimental design is shown below in Table II-C-1. PHP3528 is a non-FLP, non-GUS, BAR-expressing control plasmid. PHP687 is a control plasmid expressing R and C1 proteins, and is co-delivered to assess the efficiency of DNA delivery.

TABLE II-C-1

| Treatment # | Cell line | PHP 5096 (FLP) | PHP 687 (control) | PHP 3528 (control) | PHP 5401 (FRT) | Note |
|---|---|---|---|---|---|---|
| 1 | Transformant-1 | 1 µg | 0.5 µg | — | — | |
| 2 | Transformant-2 | 1 µg | 0.5 µg | — | — | |
| 3 | BMS-control | 1 µg | 0.5 µg | — | — | Negative control for GUS expression from input DNAs |
| 4 | Transformant-1 | — | 0.5 µg | 1 µg | — | |
| 5 | Transformant-2 | — | 0.5 µg | 1 µg | — | Controls for GUS background expression |
| 6 | BMS-control | — | 0.5 µg | 1 µg | — | |
| 7 | BMS-control | 1 µg | 0.5 µg | — | 8.5 µg | Positive control for FLP and GUS expression |
| 8 | BMS-control | — | — | — | — | Un-shot control |

As shown below in Data Table II-C-2, BMS cell lines were stably transformed with transgenic FRT-DNA sequences. These stable transformants activated GUS expression after introduction of moFLP by transient expression, confirming the results shown above in Table II-B-2.

TABLE II-C-2

| | | Input DNAs for GUS cytochemical assay and for red cell counts (C1) | | | | | | | | | | |
|---|---|---|---|---|---|---|---|---|---|---|---|---|
| | | PHP5096 + PHP687 (moFLP) | | | PHP3528 + PHP687 (control) | | | PHP5096 + PHP5401 + PHP687 (FLP/FRT control) | | | Non-shot cells | |
| Cell line | Marker | A | B | c | A | b | c | a | b | c | a | b | c |
| Transformant-1 | # GUS foci: | 1 | 0 | 0 | 0 | 0 | 0 | | | | 0 | | |
| | # Red cells: | +++ | +++ | +++ | +++ | +++ | +++ | | | | | | |
| Transformant-2 | # GUS foci: | 92 | 121 | 133 | 0 | 0 | 0 | | | | 0 | | |
| | # Red cells: | +++ | +++ | +++ | +++ | ++ | +++ | | | | | | |
| BMS | # GUS foci: | 0 | 0 | 0 | 0 | 0 | 0 | >1000 | >1000 | >1000 | 0 | 0 | 0 |
| | # Red cells: | +++ | +++ | +++ | +++ | +++ | +++ | +++ | +++ | +++ | 0 | 0 | 0 |

These data demonstrate that transiently expressed moFLP exerts recombinase activity on genomic FRT-containing DNA to catalyze site-specific excision of DNA intervening sequences between directly repeated FRT sites.

D. moFLP Versus FLPy Mediated Genomic Excision

The moFLP gene produces higher levels of site-specific excision in maize cells than FLPy. The FRT-containing BMS transformants produced in Example IIA were transfected with varied doses of FLP-expressing vectors for site specific excision of genomic transgenic sequences using the methods described above for Example II-C. Plasmids expressing FLP, PHP5095 (FLPy) and PHP5096 (moFLP) are described above for Example I-A (see Table I-A-1). The FRT/moFLP-containing PHP5849 is described above for Example I-F (see Table I-F-1). Control plasmids used were PHP3703 (non-FLP negative control; with UBI promoter and intron, wheat germ agglutinin structural gene and pinII 3' end), PHP3953 (positive control; with UBI promoter and intron, GUS structural gene and pinII 3' end), and pUC18 with no plant expression cassette used as carrier DNA to keep the total DNA load constant). Cell culture methods, DNA bombardment methods, and assay methods were those described above for Example I. The experimental design is shown below in Table II-D-20 1.

TABLE II-D-1

| Treatment # | Cell Line | PHP 5095 (FLPy) | PHP 5096 (moFLP) | PHP 5849 (moFLP/FRT) | PHP 3703 | PHP 3953 | pUC18 | Note |
|---|---|---|---|---|---|---|---|---|
| 1 | GLEAN ® Resistant BMS- FRT Transfor- mants | 0.0001 µg | | | | | 10.0 µg | |
| 2 | | 0.001 µg | | | | | 10.0 µg | |
| 3 | | 0.01 µg | | | | | 10.0 µg | |
| 4 | | 0.1 µg | | | | | 9.9 µg | |
| 5 | | 1.0 µg | | | | | 9.0 µg | |
| 6 | | 10.0 µg | | | | | | |
| 7 | | | 0.0001 µg | | | | 10.0 µg | |
| 8 | | | 0.001 µg | | | | 10.0 µg | |
| 9 | | | 0.01 µg | | | | 10.0 µg | |
| 10 | | | 0.1 µg | | | | 9.9 µg | |
| 11 | | | 1.0 µg | | | | 9.0 µg | |
| 12 | | | 10.0 µg | | | | | |
| 13 | | | | 0.0001 µg | | | 10.0 µg | |
| 14 | | | | 0.001 µg | | | 10.0 µg | |
| 15 | | | | 0.01 µg | | | 10.0 µg | |
| 16 | | | | 0.1 µg | | | 9.9 µg | |
| 17 | | | | 1.0 µg | | | 9.0 µg | |
| 18 | | | | 10.0 µg | | | | |
| 19 | | | | | 10.0 µg | | | |
| 20 | BMS Control | | | | | 0.1 µg | 9.9 µg | |
| 21 | | 1.0 µg | | | | | | |
| 22 | | | 1.0 µg | | | | | |
| 23 | | | | 1.0 µg | | | | |
| 24 | Glean ®- Resistant BMS- FRT Transfor- mants | | | | | | | Un-shot Control |
| 25 | BMS Control | | | | | | | Un-shot Control |

GUS activity indicating FLP-mediated excision of genomic DNA in cells transfected with FLYy or moFLP is shown below in Tables II-D-2 and II-D-3. The data demonstrate that the $ED_{50}$ and maximal response when moFLP is used is approximately 5-fold greater than when FLPy is used to express FLP. Significantly, the same number of excision seen with optimal levels of the Ubi::FLPy plasmid were produced with 100-fold lower plasmid dosage using Ubi-::moFLP.

TABLE II-D-2

| Treatment # (n = 3) | Mean (GUS) Blue foci per plate | Standard Deviation |
|---|---|---|
| 1 FLPy | 0 | 0 |
| 2 | 0.67 | 0.58 |
| 3 | 10.33 | 9.71 |
| 4 | 144.3 | 19.43 |
| 5 | 321.67 | 43.41 |
| 6 | 273.67 | 62.13 |
| 7 moFLP | 11.33 | 3.51 |
| 8 | 66 | 22.54 |
| 9 | 262.67 | 31.63 |
| 10 | 984 | 148.25 |
| 11 | 1245.67 | 177.75 |
| 12 | 686.33 | 93.51 |

TABLE II-D-2-continued

| Treatment # (n = 3) | Mean (GUS) Blue foci per plate | Standard Deviation |
|---|---|---|
| 13 moFLP/FRT | 0.67 | 1.15 |
| 14 | 8 | 3.61 |
| 15 | 57.33 | 18.34 |
| 16 | 493 | 85.07 |
| 17 | 1073.33 | 100.42 |
| 18 Controls | 214 | 174.79 |
| 19 | 0 | 0 |
| 20 | 1086 | 149.66 |
| 21 | 0 | 0 |
| 22 | 0 | 0 |
| 23 | 0.33 | 0.58 |
| 24 | 0 | 0 |
| 25 | 0 | 0 |

The $ED_{50}$ for each FLP expression plasmid shown in Table II-D-3 was manually determined from graphing the data.

TABLE II-D-3

| FLP expression vector | $ED_{50}$ (μg FLP expression vector) |
|---|---|
| PHP5095 FLPy | 0.13 μg |
| PHP5096 moFLP | 0.03 μg |
| PHP5849 MoFLP/FRT | 0.11 μg |

E. FLP Excision of Genomic DNA Sequences

To further evaluate site-specific excision of DNA sequences by moFLP, BMS cell lines were transformed with plasmids carrying moFLP and FRT sequences, using the methods described above for Examples I and II. Specifically, PHP5096 carrying moFLP (described above for Example I-A, see Table I-A-1) and PHP5954 carrying moFLP and FRT sequences. The FRT-containing control PHP3456 is described above for Example I-F, see Table I-F-1). The experimental design is shown below in Table II-E-1. Carrier DNA control PHP3703 is described above for Example I-D. To normalize values for GUS expression (turned on by FLP-mediated excision of an intervening sequence between promoter and structural gene) a constitutively expressed luciferase plasmid (PHP4992; UBI:Ubi intron:luciferase:pinII) was introduced at a constant amount in all treatments.

TABLE II-E-1

| Treatment # | PHP 4992 (control) | PHP 3456 (FRT) | PHP 3703 (control) | PHP 5096 (moFLP) | PHP 5954 (moFLP/FRT) | Notes |
|---|---|---|---|---|---|---|
| 1 | | | | | | Un-shot cells (negative control) |
| 2 | 1. μg | 7. μg | 2. μg | | | Negative control of GUS activity |
| 3 | 1. μg | 7. μg | 2. μg | 0.001 μg | | |
| 4 | 1. μg | 7. μg | 2. μg | 0.01 μg | | |
| 5 | 1. μg | 7. μg | 1.9 μg | 0.1 μg | | |
| 6 | 1. μg | 7. μg | 1. μg | 1. μg | | |
| 7 | 1. μg | 7. μg | | 2. μg | 0.001 μg | |
| 8 | 1. μg | 7. μg | | 2. μg | 0.01 μg | |
| 9 | 1. μg | 7. μg | | 1.0 μg | 0.1 μg | |
| 10 | 1. μg | 7. μg | | 1. μg | 1. μg | |
| 11 | 1. μg | 7. μg | | | 1. μg | Negative control (for GUS activity in PHP5954). |
| 12 | | 2.5 μg | | | 1. μg | To compare with treatment #14 |

The transformation, cell culture and assay methods were as described above for Example I. A GUS chemiluminescent assay was used following the manufacturer's protocol. In general, crude extract was incubated for one hour with Glucuron substrate at room temperature. The incubated cuvette was then inserted into an Analytical Luminescence Laboratories Model #2010 Monolight luminometer which was set to inject 100 TI Accelerator solutions, wait five seconds, then count the emitted light. The data are shown below in Table II-E-2, and are expressed as net GUS Relative Light Units (RLU) per net luciferase RLU times $10^3$.

TABLE II-E-2

| | Response [(Net GUS R.L.U./Net Luciferase R.L.U.)*$10^3$] | | |
|---|---|---|---|
| Treatment # (n = 3) | Mean | Standard deviation | Note |
| 1 | 278 | 240 | Negative control baseline. |
| 2 | −15.7 | 22.6 | Negative control |

TABLE II-E-2-continued

| | Response [(Net GUS R.L.U./Net Luciferase R.L.U.)*10³] | | |
|---|---|---|---|
| Treatment # (n = 3) | Mean | Standard deviation | Note |
| 3 | 283 | 373 | |
| 4 | 4338 | 759 | |
| 5 | 11496 | 1092 | |
| 6 | 9049 | 2443 | |
| 7 | 28.3 | 64.4 | |
| 8 | 1007 | 217 | |
| 9 | 3226 | 1438 | |
| 10 | 13521 | 2241 | |
| 11 | −6.3 | 2.9 | |
| 12 | 2327 | 261 | | moFLP expressed recombinase effectively excised DNA sequences to activate GUS (treatnents 3–6). As expected, no GUS activity was contributed by PHP5954 (treatment #11). FLP activity from transient expression of PHP5954 was shown by excision from co-delivered PHP3436 (treatments 7–10).

Example III

Transgenic Maize Cells Expressing FLP Activity

Healthy, actively growing maize cells with moFLP integrated in the genome are shown to express moFLP resulting in proper FLP-mediated site specific excision.

A. Production of FLP-containing Transformants.

A transginic maize cell line expressing FLP was prepared by inserting moFLP nucleic acid sequences into BMS cells, using materials, methods, and plasmids described above or Examples I and II. The moFLP-containing plasmid PHP5954 described above for Example II-E (see Table II-E-1) and the BAR-expressing control plasmid PHP3528 described above for Example II-C (see Table II-C-1) were used in these studies. Cells were transferred to fresh medium two days prior to bombardment, and resuspened in osmoticum one day prior to bombardment. A mass of 5 ng of each plasmid to co-transform cells.

Post-bombardment, transformants were selected for BAR expression on medium #306 containing 5 mg/ml Basta (medium #306E containing Basta commercial herbicide formulation from Agrevo, containing the active ingredient ammonium glufosinate). More than 100 Basta-R transformants were recovered. These were analyzed for FLP activity as described below in III-B.

B. Identification of FLP Expressing Events among Basta-R Transformants

Independent BMS Basta-R transformants produced in Example III-A were maintained on #306 E medium. To screen for FLP expression and activity, transformed cells were transfected with PHP3456, which contains a 1.8 kb intervening sequence between direct FRT sites (see Table I-F-1). Upon FLP-mediated excision of the intervening sequence, GUS is expressed from the plasmid in host cells.

At three days before bombardment, transformed cells (approximately 25–100 mg of each Basta-R transformant) were placed on paper filters (4 events/filter) on top of plates of #306 medium and incubated under standard conditions, as described above for Example II-B (27° C., no light). On the day of bombardment, each filter with cells was briefly dried by vacuum filtration to remove excess moisture from the filter, and then placed onto a second, dry filter in an empty Petri dish. Osmoticum (#586 medium+0.25 M sorbitol) was added and the samples were incubated for five hours before bombarding.

Bombardment conditions and methods were as described above for Examples I and II. The plasmids used included the FLP and FRT-containing PHP5954, described above for Example II-E, and PHP5096 expressing moFLP, described above for Example I-A (see Table I-A-1) as positive controls. PHP3456 expressing GUS on FLP-mediated excision is described above for Example I-F (see Table I-F-1). PHP3457, a positive control for GUS activity, is described above in Table I-F-1.

After bombardment, plates were incubated overnight at 27° C., without light, and then stained with 1 mL X-gluc buffer per plate, as described above for Examples I and II.

The experimental design is shown below in Table III-B-1.

TABLE III-B-1

| Treatment # | BMS Cell lines (n = 5 plates; with 20 independent Basta-Resistant Transformants/plate) | PHP 3456 | PHP 5096 | PHP 3457 | Notes |
|---|---|---|---|---|---|
| 1 | moFLP/FRT, Basta-R Transformants | 5 μg | | | Express GUS on FLP-mediated excision |
| 2 | moFLPlFRT, Basta-R Transformants | 5 μg | | | |
| 3 | moFLP/FRT, Basta-R Transformants | 5 μg | | | |
| 4 | moFLP/FRT, Basta-R Transformants | 5 μg | | | |
| 5 | moFLP/FRT, Basta-R Transformants | 5 μg | | | |
| 6 | Non-transgenic control | 5 μg | | | Negative control |
| 7 | Non-transgenic control | 5 μg | 1.5 μg | | Positive control FLP |
| 8 | Non-transgenic control | | | 1 μg | Positive control GUS |

Out of 100 Basta-resistant transformants obtained in Example III-A, 14 were GUS positive, indicating FLP activity:

M

| #Blue foci/event (GUS+) | Number of events |
|---|---|
| 1–10 | 3 |
| 11–50 | 3 |
| 51–100 | 6 |
| >100 | 2 |

This result provided the first evidence that transformed maize cells expressing moFLP could actively grow (divide). Positive cell lines provided hosts for retransformation, by delivery of a promoterless FRT coding sequence fusion for site-specific recombination at the FRT in the transgenic PHP5954 sequence in these cell lines.

C. Maize Cell Line Expressing FLP and Carrying an FRT Site for Self-Inactivation To obtain BMS transformants carrying moFLP and FRT sites, BMS cells were bombarded with DNA particles carrying the FRT/FLP-containing plasmid PHP5954 described above for Example II-E. The structural gene, moFLP was designed to express until a FRT::[non-FLP] sequence is recombined at the FRT site of the transgene. The control plasmid PHP3528 expressing BAR, described above for Example II-C (see Table II-C-1), was used to determine DNA transformation efficiency.

After bombardment, transformed cells were screened for resistance to bialophos (Basta-R). A total of 91 Basta-R events were isolated. Basta-R transformants were maintained on medium #306E, and then screened for FLP expression, as described below in III-D.

D. Screening BMS-FLP/FRT Transformants for FLP Activity

To screen the BMS-moFLP/FRT Basta-R transformants produced in Example III-C for FLP activity, transformed cells were transfected with PHP3456 using the procedure described above for Example III-B. On FLP-mediated excision of the 1.8 kb intervening sequence, GUS is expressed. Control plasmid PHP5954 is described in Example II-C. The silent reporter PHP3456 expresses GUS on FLP-mediated excision and is described above in Example I-F (see Table I-F-1). The control plasmid PHP687 expressing R and C 1 was used to access bombardment efficiency and is described above in Example II-B. The experimental design is shown below in Table III-D-1. For treatments 1 to 4, 5 plates were used per treatment with 4 independent transformants per plate. For treatment 5, 2 plates with 3 independent transformants per plate. Treatment 6–8 used non-transgenic control callus.

TABLE III-D-1

| Treatment # | BMS Cell Lines | PHP 3456 | PHP 5954 | PHP 687 | Notes |
|---|---|---|---|---|---|
| 1 | BMS-moFLP/FRT Basta-R | 5 μg | — | 0.01 μg | |
| 2 | BMS-moFLP/FRT Basta-R | 5 μg | — | 0.01 μg | |
| 3 | BMS-moFLP/FRT Basta-R | 5 μg | — | 0.01 μg | |
| 4 | BMS-moFLP/FRT Basta-R | 5 μg | — | 0.01 μg | |
| 5 | BMS-moFLP/FRT Basta-R | 5 μg | — | 0.01 μg | |
| 6 | Control (n = 12) | — | — | — | Non-transgenic (non-FLP) negative control |
| 7 | Control (n = 12) | 5 μg | 1 μg | 0.01 μg | Positive control |
| 8 | Control (n = 12) | | 1 μg | 0.01 μg | Negative GUS control for treatment #7 |

Out of 86 independent Basta-R transformants, eight gave blue spots (GUS+) indicating FLP expression and activity. This experiment demonstrates a viable BMS cell line expressing FLP and having FRT sites.

E. Co-Expression of FLP and a Reporter

The expression of a reporter protein from a plant transcription unit containing an FRT site at its N-terminus (PHP3457) was examined in the presence of a co-transfected plasmid expressing moFLP (PHP5096) in the embryogenic suspension cell line, 3-44-6E1. Cell culture and bombardment procedures were performed as described for Example I-E. Luciferase and GUS chemiluminescent assays were performed as described above for Examples I and II.

Plasmids used for these studies included the FLP-expressing PHP5096, described above for Example I-A (see Table I-A-1), PHP3457, the GUS+reporter plasmid having an FRT site at its N-terminus, described above for Example I-F (see Table I-F-1), PHP3703, a non-GUS, non-FLP negative control plasmid as described above for Example II-D (see Table II-D-1). A second luciferase reporter was used in this experiment to normalize DNA delivery across treatments, PHP1528, which contained the luciferase structural gene driven by the Enhanced CaMV35S promoter with Omega' and the Adh1 intron I 5' to the gene and the pinII 3' region. The experimental design os shown below in Table III-E-1.

TABLE III-E-1

| Treatment # | PHP1528 | PHP3703 | PHP5096 | PHP3457 | Notes |
|---|---|---|---|---|---|
| 1 | 1. μg | 1.1 μg | | | Negative GUS control. |
| 2 | 1. μg | 0.1 μg | 1. μg | | Negative GUS control. |
| 3 | 1. μg | 1. μg | | 0.1 μg | Positive control; benchmark for inhibition assay |
| 4 | 1. μg | | 1. μg | 0.1 μg | |

One day after bombardment, extracts were prepared and assayed for GUS and luciferase activities. After subtracting background activities for GUS and luciferase from each sample, GUS activities were then divided by respective luciferase activities, in order to normalize for variation in the efficiency of DNA delivery among replicates nd treatmints. The normalized data is shown below in Table III-E-2.

TABLE III-E-2

| Treatment # (n = 3) | Mean GUS+ | Standard deviation |
|---|---|---|
| 1 | −11.5 | 1.7 |
| 2 | −30.0 | 11.0 |
| 3 | 412.1 | 23.6 |
| 4 | 470.7 | 18.7 |

(1981) *Nucl. Acid Res.* 9:2871–2888). The 79 bp Tobacco Mosaic Virus leader (Gallie et al. (1987) *Nucl. Acid Res.* 15:3257–3273) was inserted downstream of the promoter followed by the first intron of the maize alcohol dehydrogenase gene ADH1-S (Dennis et al. (1984) *Nucl. Acid Res.* 12:3983–3990). The pinII terminator was ligated downstream to create the BAR expression cassette. PHP8007 also contains the modified FLP gene driven by the promoter region of the maize ubiquitin gene Ubi-1 (Christensen et al. (1992) *Plant Mol. Biol.* 18:675–689). The pinII terminator was ligated downstream to create the FLP expression cassette. PHP8007 and other FLP and FRT-containing plasmids used in transformation of embryogenic maize events are listed in Table IV-A-1 below.

TABLE IV-A-1

Plasmids used to verify FLP activity and FRT sites in regenerable maize callus, regenerated plants and progeny.

| PHP | Promotor | 5' intron | Structural Gene | 3' sequence | Purpose |
|---|---|---|---|---|---|
| Plasmids containing FLP recombinase expression-cassette; | | | | | |
| 5096 | UBI | Ubi-intron | moFLP | pinII | Maize-optimized |
| 5954 | UBI | Ubi-intron/FRT | moFLP | pinII | Maize-optimized |
| 8007 | UBI | Ubi-intron | moFLP | pinII | Maize-optimized |
| Plasmids Containing FRT sequences to demonstrate excision of bar and activation of GUS. | | | | | |
| 5869 | Enhanced 35S | adhI-intron/FRT | bar | pinII/FRT :GUS::pin II | Excision of bar gene from stably integrated genomic locus |

These data demonstrate transient expression and activity of FLP does not effect co-expression of a reporter containing an FRT site fused to its coding sequence.

Example IV

FRT Recombination in Regenerable Maize Callus and Plants and Expression of Modified FLP Encoded Recombinase in Maize Callus and Plants A. FLP and FRT Plasmid DNA Construction FLP vectors were constructed using standard molecular biology techniques (Sambrook et al. eds.). The plasmid PHP8007 is described, but the other vectors used in these experiments contain combinations of the same basic regulatory elements. Plasmid PHP8007 contains a selective marker gene, bar (Thompson et al. (1987) *EMBO J* 6:2519–2523) driven by a Cauliflower Mosaic Virus 35S promoter with a duplicated enhancer region (Gardner et al.

B. Preparation of Callus with Integrated FRT-containing Sequences

Hi-II germplasm, a maize genotype with a high frequency and vigor of type II culture initiation was selected out of an A188×B73 cross (see Armstrong et al. (1991) *Maize Genetics Newsletter* 65:92–93) and is publicly available.

FRT recombination in regenerable maize callus and plants was evaluated by the stable transformation of the plasmid PHP5869 into embryogenic callus cultures of the genotype Hi Type II (Hi-II). Rapidly growing embryogenic callus was suspended in liquid medium and sieved through a 860 urn screen. Approximately 250 mg fresh weight of sieved callus was then suspended in 5 ml of medium and evenly distributed onto a 5.5 cm glass fiber filter disk using vacuum filtration on a 4.7 cm microanalysis holder. DNA was delivered into the cells using the Biorad PDS-1000 biolistics apparatus. Precipitation of plasmid DNA onto 1.0 um tungsten particles was as described by Klein et al. (1988) *Proc. Nat. Acad. Sci.* 85:4305–4309. Post-bombardment selection for cells expressing the bar gene was done essentially as described in Register et al. (1994) *Plant Mol. Biol.* 25:951–961; following bombardment, the filter disk and cells were transferred to callus culture medium for 7 days after which the filter disk and cells were transferred to fresh callus culture medium containing 3 mg/l bialaphos (callus culture medium and regeneration media were similar to those described by Armstrong (1994) in "The Maize Handbook", Freeling and Walbot, eds. Springer-Verlag, New York, pp663–671). After another 7 days the cells were removed from the filter disk and suspended in 5 ml of selection medium (held at 37° C.) containing 0.6% (w/v) low melting point agarose (Sea-Plaque; FMC, Inc.). The suspension was divided into 2 equal aliquots and each aliquot was evenly plated over solidified medium in 100×15 mm Petri dishes. After 4–6 weeks, rapidly growing putative transformed calli were removed and transferred to the surface of fresh selection medium.

The accessibility and finctionality of the FRT sites was evaluated by transiently expressing FLP recombinase in the callus using particle delivery of the recombinase DNA. Cell preparation and DNA delivery was as described above. The target sequence contained in PHP5869 was constructed such that recombination of the FRT sites within the sequence would result in excision of the bar gene and expression of the scorable marker GUS. A total of 25 putative events containing PHP5869 were tested for FRT recombination.

TABLE IV-B-2

| Event Number | Recombination Score |
|---|---|
| 776.71-47-1 | +++ |
| 776.77-68-1 | ++ |
| 776.83-19-1 | ++ |
| 776.85-21-1 | +++ |
| 776.89-17-4 | ++++ |
| 776.89-17-6 | +++ |
| 776.89-17-7 | +++ |
| 776.89-19-1 | ++++ |
| 776.89-19-3 | +++ |
| 776.89-19-5 | ++++ |
| 776.89-19-10 | +++ |
| 776.89-20-1 | +++ |

C. Evaluation of FRT Events in Progeny

A second set of tests were performed to evaluate PHP5869 stable transformed calli (from progeny seed, but using the method described above) and progeny embryos. These calli and embryos derived from the different transformation events were bombarded with PHP8007 plasmid DNA. Transient FLP gene expression (from plasmid PHP8007) catalyzed excision of bar and resulted in activation of the GUS gene in PHP5869 stable transformed cells. The level of GUS expression and the density of GUS staining in these cells were used to evaluate the "quality" of PHP5869 transformed events. The results are reported in Table IV-C-1. For results of bombardment of PHP6869 transformants with PHP8007:

TABLE IV-C-1

| | | Embryo Bombardment | | | | Callus Bombardment | | | |
|---|---|---|---|---|---|---|---|---|---|
| Event No. | Pedigree | Total | GUS+ | % | GUS Density | Total | GUS+ | % | GUS Density |
| 776.89-17-6 | T0xGS3 | 40 | 3 | 8% | + | 6 | 4 | 67% | + |
| 776.89-17-7 | T0xGS3 | 143 | 32 | 22% | + | 25 | 13 | 52% | ++ |
| 776.89-17-7 | T0 self | 38 | 10 | 26% | ++ | 18 | 3 | 17% | ++ |
| 776.89-19-1 | T0xGS3 | 54 | 28 | 52% | +++ | 11 | 10 | 91% | +++ |
| 776.89-19-3 | T0xGS3 | 39 | 9 | 23% | +++ | 23 | 21 | 91% | ++ |
| 776.89-19-3 | T0 self | 30 | 9 | 30% | +++ | 3 | 3 | 100% | ++ |
| 776.89-19-5 | T0xGS3 | 47 | 31 | 66% | +++ | 67 | 60 | 90% | +++ |
| 776.89-19-5 | T0 self | 92 | 36 | 39% | +++ | 25 | 21 | 84% | +++ |
| 776.89-20-1 | T0xGS3 | 57 | 19 | 33% | +++ | 16 | 15 | 94% | ++ |
| 776.89-20-1 | T0 self | | | | | 15 | 15 | 100% | ++ |

The recombination potential of the events was scored by visual observation of the number of GUS-expressing foci which could be observed after exposure of the cells to GUS substrate 3 days after bombardment. The results are summarized in Table IV-B-1 below.

For relative level of recombination with PHP5869 events:

TABLE IV-BA-1

| Recombination Score | None(−) | + | ++ | +++ | ++++ |
|---|---|---|---|---|---|
| Percent of Events | 32% | 8% | 12% | 36% | 12% |

+ = 1 to 5 blue spots; ++ = 5–25; +++ = 25–100; ++++ = >100 spots per plate

As the data above demonstrate, a high percentage of transformation events exhibited high levels of FLP-induced excision. Of the events that exhibited recombination, 12 were regenerated for analysis at the whole plant level (Table IV-B-2). For events exhibiting FLP-mediated recombination that were regenerated for further analysis:

The bombardment results shown in Table IV-C-1 confirmed three things: 1) FLP recombinase can catalyze site-specific recombination at FRT sites in the maize genome, the functionality of FRT sequences is heritable in maize, and 3) there are differences in recombination frequency and GUS expression between FRT events. These difference may reflect the "quality" of the FRT events for site specific recombination, and were also observed in the F1's of FRT×FLP (see below).

D. FLP Gene Transformation and Evaluation of FLP Activity

Transformation of the FLP plasmid DNA, PHP8007, in Hi-II followed the standard Hi-II bombardment transformation protocol (Songstad D. D. et al. (1996) *In Vitro Cell Dev. Biol. Plant* 32:179–183). Cells were transformed by culturing maize immature embryos (approximately 1.5 mm in length) onto 560P medium containing N6 salts, Erikkson's vitamins, 0,69 g/l proline, 2 mg/l 2,4-D and 3% sucrose. After 4–5 days of incubation in the dark at 28° C., embryos were removed from 560P medium and cultured, coleorhizal end up, onto 560 L medium which is equivalent to 560P but contains 12% sucrose. Embryos were allowed to acclimate to this medium for 3 h prior to transformation. Embryos were transformed using the PDS-1000 Helium Gun from Bio-Rad at one shot per sample using 650PSI rupture disks. DNA delivered per shot averaged at 0.0667 ug. Following bombardment, all embryos were maintained on 560L medium for 48 hours before transfer to 3% sucrose and 3 mg/l bialaphos. Plates were maintained at 28° C. in the dark and were observed for colony recovery with transfers to fresh medium occurring every two weeks. Transgenic colony recovery was noted initially as growing callus tissue with a healthy phenotype on selection.

The transformed calli were evaluated for FLP activity, callus morphology and plant regeneration ability to determine whether the FLP activity affects callus formation and plant regeneration.

FLP activity was evaluated by bombarding PHP5869 plasmid DNA into PHP8007-transformed calli. The bombarded calli were cultured for 2 to 3 days under normal culture condition and then stained with X-gluc to score GUS gene expression. If the FLP gene was expressing, it would recombine the FRT sites in plasmid PHP5869, resulting in excision of bar and connection of the GUS gene to the 35S promoter to activate GUS. If the FLP gene was more active in a particular transformed callus, more dark blue cells would be observed.

Callus morphology was evaluated by examining the proportion of somatic embryos in each of the embryo-derived calli. Callus containing more somatic embryos would be capable of generating more plants.

The ability of calli to regenerate plants was evaluated by tabulating the number of plants produced from each of the embryo-derived calli. A single embryo-derived callus producing more than 15 plants was given the highest score. Progressively lower scores were given to calli producing 11–15 plants, 6–10 plants, 1–5 plants or no plants. Each characteristic was evaluated using a scale with 4 representing the best (or highest) rating and 1 representing a low level, while 0 represented an absence of that characteristic. Results of this evaluation are reported below in Table IV-D-1.

For evaluation results of FLP transformed calli:

TABLE IV-D-1

| FLP Activity | Total Events | Callus morphology | | | Plant regeneration Event | | |
|---|---|---|---|---|---|---|---|
| | | Score | Event No. | % | Score | No. | % |
| 4 | 30 | 4 | 4 | 13.3% | 4 | 7 | 23.3% |
| | | 3 | 5 | 16.7% | 3 | 3 | 10.0% |
| | | 2 | 10 | 33.3% | 2 | 3 | 10.0% |
| | | 1 | 11 | 36.7% | 1 | 7 | 23.3% |
| | | 0 | 0 | 0.0% | 0 | 10 | 33.3% |
| 3 | 21 | 4 | 1 | 4.8% | 4 | 2 | 9.5% |
| | | 3 | 2 | 9.5% | 3 | 4 | 19.0% |
| | | 2 | 13 | 61.9% | 2 | 3 | 14.3% |
| | | 1 | 5 | 23.8% | 1 | 8 | 38.1% |
| | | 0 | 0 | 0.0% | 0 | 4 | 19.0% |
| 2 | | 4 | 0 | 0.0% | 4 | 0 | 0.0% |
| | | 3 | 2 | 22.2% | 3 | 0 | 0.0% |
| | | 2 | 1 | 11.1% | 2 | 0 | 0.0% |
| | | 1 | 6 | 66.7% | 1 | 1 | 11.1% |
| | | 0 | 0 | 0.0% | 0 | 8 | 88.9% |
| 1 | 11 | 4 | 0 | 0.0% | 4 | 0 | 0.0% |
| | | 3 | 3 | 27.3% | 3 | 2 | 18.2% |
| | | 2 | 4 | 36.4% | 2 | 1 | 9.1% |
| | | 1 | 4 | 36.4% | 1 | 1 | 9.1% |
| | | 0 | 0 | 0.0% | 0 | 7 | 63.6% |
| 0 | 11 | 4 | 2 | 18.2% | 4 | 4 | 36.4% |
| | | 3 | 3 | 27.3% | 3 | 1 | 9.1% |
| | | 2 | 5 | 45.5% | 2 | 2 | 18.2% |
| | | 1 | 1 | 9.1% | 1 | 3 | 27.3% |
| | | — | — | — | 0 | 1 | 9.1% |

Even in events not expressing FLP (category 0 under FLP activity), a wide range of callus morphologies and regeneration capacities were observed. As FLP activity increases to the highest level observed, the variability in callus quality and regeneration appears to remain high and no apparent correlation can be discerned.

To verifiy the effect of the FLP activity on transgenic plant fertility, pollen morphology and female gamete fertility were evaluated. Pollen morphology was used as an indicator for pollen viability. The pollen morphology results are reported in Table IV-D-2. The results in Table IV-D-2 demonstrate that FLP activity had some negative impact on pollen viability. For events with higher FLP activity in T0 plants, the percentage of events with normal pollen was lower. However, the data also showed that in the events with highest (4) FLP activity in T0 plants, there were still 26.7% of the transgenic events whose pollen appeared normal.

TABLE IV-D-2

| FLP acitivity | No. of Events | Plants with Normal Pollen | | Plants with 50% Normal Pollen | | Plants with Mixed Pollen* | |
|---|---|---|---|---|---|---|---|
| | | Event No. | % | Event No. | % | Event No. | % |
| 4 | 12 | 4 | 26.7% | 9 | 60.0% | 2 | 13.3% |
| 3 | 12 | 6 | 50.0% | 5 | 41.7% | 1 | 8.3% |
| 2 | 0 | 0 | | 0 | | 0 | |
| 1 | 1 | 1 | | 0 | 0.0% | 0 | 0.0% |
| 0 | 6 | 3 | 50.0% | 0 | 0.0% | 3 | 50.0% |

*Plants with mixed pollen is a group of T0 plants that were regenerated from the same embryo-derived callus. Some plants showed normal pollen and others had 50% normal pollen. Southern analysis showed that the plants with different morphologies of pollen represent different transformation events.

Female gamete fertility can be determined by observing T1 seed formation following crosses made between FLP T0 plants as the female parent and non-transformed plants as the male parent. If the FLP-containing female gamete showed normal inheritance, about 50% of the T1 seeds should contain the FLP gene. If FLP expression has a negative impact on female fertility, less than 50% of the T1 seeds should have the FLP gene. FLP activity in the T1 seeds was assayed by bombarding PHP5869 into T1 embryos as described above for FLP callus bombardment. T1 seed bombardment results are reported in Table IV-D-3.

For FLP T1 seeds bombardment with PHP5869:

TABLE IV-D-3

| FLP activity in T0 generation | Total events | Pollen Morphology | Total seeds bombarded | Seeds with FLP+ No. | Seeds with FLP+ % | Seeds with FLP− No. | Seeds with FLP− % |
|---|---|---|---|---|---|---|---|
| 4 | 3 | normal | 300 | 146 | 49% | 154 | 51% |
| 4 | 6 | 50% normal | 226 | 48 | 21% | 178 | 79% |

As shown in Table 6, the 300 seeds derived from 3 events that have normal pollen showed 49% FLP+ and 51% FLP−. This segregation is very close to Mendelian 1:1 ratio. In these events, the FLP activity does not reduce the fertility of the female gametes. On the other hand, the 226 seeds derived from 6 events that have 50% normal pollen showed 21% FLP+ and 79% FLP−. In these events, the FLP activity does reduce the fertility of the female gametes. In addition, an average of 130 seeds were formed on each of the 5 T0 plants (3 events) that have normal pollen, while an average of 20 seeds were formed on each of the 14 T0 plants (6 events) that have 50% normal pollen. In non-transformed Hi-II, there are usually 100–150 seeds formed on most of the ears. These data confirmed that the kernel formation (female gamete fertility) is not reduced in those T0 plants with normal pollen, but is reduced in those T0 plants with 50% normal pollen.

Combining the data in both Table IV-D-2 and Table IV-D-3, it appeared that FLP activity influenced both male and female gametes in maize, and this effect was usually observed in the same plants. However, this effect does not reduce the utility of the FLP system in maize because about 27% of the transgenic events showed high FLP activity and both male and female gametes were normal.

These data suggested that evaluation of plant fertility in FLP-containing events before using them is one of the key steps for successful application of this system in maize. If negative effects occur in certain plants, it will usually affect both male and female gametes. We can use the T0 pollen evaluation technique to quickly and easily determine the affected and non-affected plants.

DNA from T0 plants recovered following stable transformation with the FLP recombinase gene was subjected to Southern analysis using standard techniques. Many of the plants contained DNA bands corresponding to both FLP and bar genes. FLP activity appeared to be related to Southern patterns. Usually, events with a low copy number of the gene and a simple insertion pattern gave rise to high FLP activity. However, the correlation between Southern patterns and the effect of FLP activity on the fertility of gametes is not clear.

E. Evaluation of the F1 Generation

The purpose of making F1 crosses between FLP plants and FRT plants is to bring FLP and FRT together in the same genome and then to evaluate FRT site-specific recombination catalyzed by FLP recombinase. FRT site-specific recombination results in the excision of FRT::bar::PIN-II::FRT and activation of a GUS gene. Thus, the GUS gene was used as the visible marker to identify FLP recombinase catalyzed site-specific recombination in the F1. F1 crosses were made using either FLP-expressing plants as a female and FRT/bar/GUS-containing plants as the male. Reciprocal crosses were made also. F1 seeds were collected from these crosses and among 1,412 germinated plants, 1031 plants or 73% of the total plants were Ignite positive, indicating expression of the bar gene (tested by painting a 2% solution of Ignite onto the leaves; Ignite is a commercial herbicide from AgrEvo containing the active ingredient ammonium glufosinate). This value is very close to the 75% expected from 3:1 segregation. Among those 1,412 plants, theoretically, 25% or 353 plants should contain both FLP recombinase and FRT/Bar/GUS DNA in the same plants. Only these 353 plants containing both DNA sequences (a FLP expression cassette and FRT sites) could potentially catalyze site-specific recombination to activate GUS. Leaf tissues collected from all Ignite positive plants were stained with X-gluc to assay for GUS expression. 197 plants expressed GUS. The range of levels of GUS expression in F1 plants ranged from no expression to high levels, and varied from event to event. On average, the frequency was 55.8%. These results demonstrated that the nucleic acid sequence encoding FLP can be transmitted and is active in subsequent generations for site-specific recombination. Furthermore, events containing a genomic FLP expression cassette and genomic FRT sites can be crossed to effect excision of the FRT-flanked sequence.

All GUS expressing F1 plants were subjected to PCR analysis to confirm bar gene excision. One primer was designed within the 35S promoter region and a second primer was within the GUS gene. Excision of the bar gene should yield a PCR fragment of 250 bp, as compared to a 1350 bp expected if the bar gene is not excised. The PCR assays confirmed that all GUS expressing F1 plants had a 250 bp band.

In the F1 crosses, only the events with high FLP activity (scored as 3 and 4, see Table IV-D-1) that had normal pollen in their T0 plants were used and the recombination frequency mainly depended on the quality of FRT events. Some comparisons of the recombination frequency in different crosses are listed below in Table IV-E-1. When FLP event 260891 was used for the F1 crosses, different FRT events used in the F1 crosses resulted in different recombination frequencies. For example, when FRT events 776.89–19–3 and 776.89–20–1 were used, the recombination frequency was 100% in the F1 plants, while if 776.89–17–6 and 776.89-17-7 were used for the F1 crosses, the recombination frequencies were about 40% in the F1 plants. If FRT event 776.89-19-1 was used for the F1 cross, no recombination was observed in the resulting F1 plants.

For recombination frequency in different F1 crosses:

TABLE IV-E-1

| FLP Event | FRT event | Recombination frequency in F1 cross |
|---|---|---|
| 260891 | 776.89-17-6 | 41% |
| 260891 | 776.89-17-7 | 40% |
| 260891 | 776.89-19-1 | 0% |

TABLE IV-E-1-continued

| FLP Event | FRT event | Recombination frequency in F1 cross |
|---|---|---|
| 260891 | 776.89-19-3 | 100% |
| 260891 | 776.89-19-5 | 92% |
| 260891 | 776.89-20-1 | 100% |

In the F1 crosses, both FRT and FLP were used as either male or female parents. The evaluation results demonstrated that in general, the recombination frequency in the F1 plants was higher if FLP events were used as the female parent, as opposed to using the FRT events as the female parent. Table IV-E-2 provides a few examples of this comparison.

For recombination frequency in the reciprocal crosses between FLP and FRT:

TABLE IV-E-2

| Event as Female Crosses | Event as Male in F1 Crosses | F1 Plants Ignite+ | Gus+ | Recombination |
|---|---|---|---|---|
| FRT/776.89-19-1 | FLP/260935 | 22 | 1 | 14% |
| FLP/260935 | FRT/776.89-19-1 | 28 | 7 | 75% |
| FRT/776.89-19-3 | FLP/260935 | 12 | 3 | 75% |
| FLP/260935 | FRT/776.89-19-3 | 13 | 0 | 0 |
| FRT/776.89-19-5 | FLP/260935 | 31 | 1 | 10% |
| FLP/260935 | FRT/776.89-19-5 | 39 | 6 | 46% |
| FRT/776.89-20-1 | FLP/260935 | 25 | 4 | 48% |
| FLP/260935 | FRT/776.89-20-1 | 34 | 8 | 71% |
| FLP as male | | 90 | 9 | 30% |
| FLP as female | | 114 | 21 | 55% |

In Table IV-E-2, Ignite+ indicates Ignite resistant plants among the F1 plants. Theoretically, one third of the Ignite resistant F1 plants contained both FLP and FRT constructs in the same plants. Only this fraction (⅓) that contain both FLP and FRT had the potential for site-specific recombination. The recombination frequency in the last column in Table IV-E-2 was calculated based on this estimate. The data in Table IV-E-2 demonstrated that the recombination frequency was higher when the FLP containing events were used as the female rather than as the male (in 3 out of 4 F1 crosses). On average, the recombination frequency was 55% in the crosses where FLP expressing plants were used as the female parents, while the frequency was 30% in the reciprocal crosses. One explanation is that in maize, as in most plants, the cytoplasm in the zygote is inherited from the female gamete, and sperm cells carry little cytoplasm to the fertilized zygotes. In the case where FLP expressing plants were used as a female parent, the existing FLP recombinase made in the female cytoplasm may bind to the FRT sites brought in by male gametes immediately and catalyze excision rapidly. In the reciprocal case FLP protein synthesis would have to start anew after fertilization, thereby delaying excision. In the GUS expressing F1 plants, uniform GUS staining of the leaf tissues collected from three leaves in a single plant was common, although some chimeric GUS expressing plants were observed. Uniform GUS staining indicated that the site-specific recombination occurred most likely at the single cell stage of the zygote while the chimeric GUS expressed plants could result from either later bar gene excision or GUS gene silencing (Flavell (1994) Proc. Natl. Acad. Sci. USA vol. 91, 3490–3496); Matzke and Matzke (1995) Plant Physiol. 107:679–685); Matzke and Matzke (1995) TIG, vol. 11, no. 1, 1–3). These two possibilities can be distinguished by PCR assays. If both GUS-expressing tissue and non-GUS expressing tissue from the same plants contain the 250 bp PCR band, this non-GUS expressing sector(s) is likely the result of GUS gene silencing. On the other hand, if the 250 bp PCR band can be found in the GUS expressing sector(s), and a 1,350 bp band is found in the non-GUS expressing sector(s), this chimera is due to later recombination in this plant.

F. Evaluation of the F2 Generation

The F1 plants expressing GUS were pollinated by non-transformed pollen to generate F2 seeds. The F2 generation was evaluated for segregation of the genes. Normally, four different genotypes are expected in the F2, i.e. FLP+/BAR+, GUS+/BAR−, FLP+/BAR+/GUS+ and FLP−/BAR−/GUS− and they should segregate in a 1:1:1:1 ratio. These four genotypes were phenotypically either Ignite+ or Bialaphos+/GUS− (FLP+/BAR+), Ignite− or Bialaphos−/GUS+ (GUS+/BAR−), Ignite+ or Bialaphos+/GUS+ (FLP+/BAR+/GUS+) and Ignite− or Bialaphos−/GUS− (FLP−/BAR−/GUS−). The F2 embryos were placed on medium for callus initiation and then the callus from each embryo was divided into three parts, one was used for GUS staining to verify the GUS expression, one was used for culturing on Bialaphos containing medium to verify bar expression and one was kept on the same medium used for callus initiation. Embryos from 4 F1 plants were assayed with this method and the results are reported in Table IV-F-1.

For F2 embryo segregation:

TABLE IV-F-1

| F1 Plant | Total F2 embryos | GUS+/Bialaphos+ | | GUS−/Bialaphos+ | | GUS+/Bialaphos− | | GUS−/Bialaphos− | |
|---|---|---|---|---|---|---|---|---|---|
| | | No. | % | No. | % | No. | % | No. | % |
| 27-14 | 69 | 17 | 24.6% | 15 | 21.7% | 19 | 27.5% | 18 | 26.1% |
| 28-10 | 54 | 8 | 14.8% | 13 | 24.1% | 11 | 20.4% | 22 | 40.7% |
| 28-13 | 46 | 9 | 19.6% | 7 | 15.2% | 14 | 30.4% | 16 | 34.8% |
| 33-10 | 92 | 28 | 30.4% | 21 | 22.8% | 26 | 28.3% | 17 | 18.5% |
| Sum | 261 | 62 | 23.7% | 56 | 21.5% | 70 | 26.8% | 73 | 28.0% |

Data in Table IV-E-2 showed an expected segregation in F2 calli. F2 plants were also used for this evaluation. The F2 plants in a field were painted with 1% Ignite to verify bar expression and leaf-punches from all the F2 plants were stained with X-gluc to verify GUS expression. The results were reported in Table IV-F-2. The 4 expected phenotypes were observed in this F2 population.

For F2 plant segregation:

TABLE IV-F-2

| F1 Plant | Total F2 Plants | GUS+/Ignite+ No. | % | GUS+/Ignite+ No. | % | GUS+/Ignite– No. | % | GUS–/Ignite– No. | % |
|---|---|---|---|---|---|---|---|---|---|
| 26-2 | 19 | 4 | 21.1% | 4 | 21.1% | 7 | 36.8% | 4 | 21.1% |
| 26-21 | 20 | 4 | 20.0% | 8 | 40.0% | 6 | 30.0% | 2 | 10.0% |
| 27-17 | 20 | 6 | 30.0% | 7 | 35.0% | 4 | 20.0% | 3 | 15.0% |
| 28-19 | 17 | 5 | 29.4% | 4 | 23.5% | 4 | 23.5% | 4 | 23.5% |
| 32-6 | 18 | 7 | 38.9% | 4 | 22.2% | 3 | 16.7% | 4 | 22.2% |
| 37-17 | 19 | 2 | 10.5% | 10 | 52.6% | 3 | 15.8% | 4 | 21.1% |
| 64-10 | 19 | 3 | 15.8% | 6 | 31.6% | 2 | 10.5% | 8 | 42.1% |
| 64-12 | 17 | 2 | 11.8% | 5 | 29.4% | 2 | 11.8% | 8 | 47.1% |
| Sum | 149 | 33 | 22.1% | 48 | 32.2% | 31 | 20.8% | 37 | 24.8% |

The F2 leaf tissues from these 4 classes will be subjected to Southern analysis to confirm their genotype at the molecular level.

G. FLP-mediated FRT Excision in the Meristem to Produce Large Chimeric Sectors

In addition to showing FLP-mediated transgene excision in suspension cells, callus and immature embryo cells (and progenitor cells), we also demonstrated efficient excision in meristem tissue to produce heritable somatic sectors. F3-generation immature embryos from the original event 776.89-19-5 were used as starting material. Ears were harvested 9–10 days after pollination, when the embryos were at the coleoptilar stage of development. At this point, the apical meristem is exposed for DNA delivery. A total of 330 coleoptilar-stage embryos were placed onto MS-based medium with 15% sucrose. After sitting on this medium at 27° C. overnight in the dark, the meristems were bombarded with PHP5096. DNA precipitation was done using 1.0 um tungsten particles using standard methods (see Klein et al, ibid). Bombardment was done using a Biorad PDS-1000 with the stage set at a distance of 10 cm from the accelerator stopping screen, using a vacuum of 28 mm Hg. Approximately 1.6 ug DNA was used per shot. After bombardment, the embryos were placed back onto MS medium+15% sucrose which promotes embryo maturation. After one week, the embryos were moved onto MS+3% sucrose for germination and moved into lighted growth chambers. As the plants grew, leaf samples were taken and assayed for GUS activity using published methods for GUS histochemical staining (Jefferson (1987)). A total of 29 plants had large sectors and were taken to the greenhouse for further analysis. In 8 of these plants, the sectors appeared to stop (which is consistent with fate development studies), but in 21 plants the sectors persisted into the mature plant. Non-sectored control plants (bombarded without DNA) exhibited the unaltered transgenic phenotype of this event; i.e. all leaves were Basta-resistant and GUS-negative (no staining). FLP-induced sectors had lost Basta-resistance and were now sensitive, and had gained positive GUS expression (blue staining). Nine plants had large, persistent sectors that went all the way into the tassel, and all 9 of these transmitted the "excision-phenotype" to their progeny through the chimeric tassel. Six plants in this group also had sectors running through the ear, and transmitted through seed. This represents almost a 3% transmission frequency of the bar-excised/GUS-activated locus through somatically induced chimeric sectors into progeny.

This result demonstrated that FLP-mediated excision is efficient when FLP is expressed in the meristem, and this can produce large "excision-sectors" in the resultant plants.

H. Overall Conclusions for Evaluation of Stable Expression in Plants.

From the above data, it can be concluded that FLP recombinase has been successfully used for site-specific recombination in maize. This has been demonstrated in callus, in scutellar cells of immature embryos and in the meristem. Based on these studies, it is expected that FLP-mediated excision would work in all maize tissues in which FLP is expressed. The utility of inherited FLP activity and accessible FRT-flanked loci in the genome have also been demonstrated.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

We claim:

1. A nucleotide sequence encoding an FLP recombinase wherein said sequence comprises the DNA sequence set forth in SEQ ID NO: 1.

2. A method for excising a target nucleotide sequence in a plant cell, said method comprising introducing a nucleotide sequence modified for enhanced expression in a plant, said modified sequence comprising the DNA sequence set forth in SEQ ID NO: 1, wherein said target sequence is flanked by FRT sites.

3. The method of claim 2 wherein said plant is a dicot.
4. The method of claim 2 wherein said plant is a monocot.
5. The method of claim 4 wherein said monocot is maize.
6. A transformed plant containing within its genome a nucleotide sequence encoding an FLP recombinase wherein said sequence comprises the DNA sequence set forth in SEQ ID NO: 1.
7. The plant of claim 6 wherein said plant is a dicot.
8. The plant of claim 6 wherein said plant is a monocot.
9. The plant of claim 8 wherein said monocot is maize.

10. Seed of the plant of claim 6.
11. Seed of the plant of claim 7.
12. Seed of the plant of claim 8.
13. The plant of claim 6 wherein said plant further comprises integrated FRT sites in its genome.
14. Seed of the plant of claim 13.
15. A plant cell produced by the method of claim 2.
16. A plant regenerated from the plant cell of claim 15.
17. The plant of claim 16 wherein said plant is a maize plant.
18. Seed of the plant of claim 17.

* * * * *

UNITED STATES PATENT AND TRADEMARK OFFICE
CERTIFICATE OF CORRECTION

PATENT NO. : 5,929,301
DATED : July 27, 1999
INVENTOR(S) : Baszczynski et al.

It is certified that error appears in the above-identified patent and that said Letters Patent is hereby corrected as shown below:

On the Title Page:
In the Inventor's names, "Baszcynski" should read --Baszczynski--.

In the Inventor's names, please add a ninth inventor --Grace Marie St. Clair, Des Moines,--.

In the "References Cited", under "Other Publications", line 1, "639-652" should read -- 637-652 --.

In the "References Cited", under "Other Publications", line 2, ""Acid" should read -- Acids--.

In the "References Cited", under "Other Publications", line 4, before "plant" please insert --the--.

In the "References Cited", under "Other Publications", after line 4, please insert --July 1990--.

Signed and Sealed this

Third Day of April, 2001

Attest:

NICHOLAS P. GODICI

*Attesting Officer*   *Acting Director of the United States Patent and Trademark Office*